(12) United States Patent
Galler et al.

(10) Patent No.: US 6,589,522 B1
(45) Date of Patent: Jul. 8, 2003

(54) VACCINES AGAINST INFECTIONS CAUSED BY YF VIRUS; YF INFECTIOUS CDNA, METHOD FOR PRODUCING A RECOMBINANT YF VIRUS FROM THE YF INFECTIOUS CDNA AND PLASMIDS TO ASSEMBLE THE YF INFECTIOUS CDNA

(75) Inventors: Ricardo Galler, Niteroi (BR); Marcos Da Silva Freire, Niteroi (BR)

(73) Assignee: Fundacao Oswaldo Cruz-Fiocruz, Rio de Janeiro (BR)

( * ) Notice: Subject to any disclaimer, the term of this patent is extended or adjusted under 35 U.S.C. 154(b) by 0 days.

(21) Appl. No.: 09/705,949

(22) Filed: Nov. 6, 2000

Related U.S. Application Data

(62) Division of application No. 09/058,411, filed on Apr. 10, 1998, now Pat. No. 6,171,854.

(30) Foreign Application Priority Data

Apr. 11, 1997 (BR) .............................................. 9701774

(51) Int. Cl.$^7$ ............................................... A61K 39/12
(52) U.S. Cl. ................... 424/93.2; 424/93.6; 424/218.1; 435/235.1; 435/239
(58) Field of Search ............................. 424/93.2, 93.6, 424/218.1; 435/235.1, 239

(56) References Cited

U.S. PATENT DOCUMENTS 4,719,177 A 1/1988 Baltimore et al.
6,171,854 B1 1/2001 Galler et al.

FOREIGN PATENT DOCUMENTS

WO     WO 93/06214     4/1993

OTHER PUBLICATIONS

Stedman's Medical Dictionary, 27th Edition, Lippincott Williams & Wilkins 2000, www.pdrel.com/pdr/.*
Theiler, M. and Smith, H.H. (1937), "The effect of prolonged cultivation in vitro upon the pathogenicity of yellow fever virus", J. Exp. Med. 65:767–786.
Rice, C.M.; Lenches, E.; Eddy, S.R.; Shin, S.J.; Sheets, R.L. and Strauss, J.H. (1985), "Nucleotide sequence of yellow fever virus; implications for flavivirus gene expression and evolution". Science 229:726–733.
Despres, P.; Cahour, A.; Dupuy, A.; Deubel, V.; Bouloy, M. Digoutte, J.P.; Girard, M. 91987), "High genetic stability of the coding region for the structural proteins of yellow fever strain 17D", J. Gn. Virol. 68:2245–2247.
Duarte dos Santos, C.N., Post, P.R., Carvalho, R. Ferreira, I.I., Rice, C.M., Galler, R. (1995). Complete nucleotide sequenxe of yellow fever virus vaccine strains 17DD and 17D–213. Virus Research 35:35–41.

Hahn, C.S.; Dalrympie, J.M.; Strquss, J.H. and Rice, C.M. (1987). "Comparison of the Virulent Asibi strain of yellow fever virus with the 17D vaccine strain derived from it". Proc. Natl. Acad. Sci. USA 84:2029–2033.
Rey, F.A.; Heinz F.X.; Mandl, C.; Kunz, C and Harrison, S.C. (1995), "The envelope glycoprotein from tick–borne encephalitis vius at 2A resolution". Nature 375:291–298.
Mandl, M.W.; Guirakhoo, F.; Holzmann, H.; Heinz, F.X. and Kunz, C. (1989). "Antigenic structure of the flavivirus envelope E protein at the molecular level using tick–borne encephalitis virus as a model". J. Virol. 63:564–571.
Lepiniec, L.; Dalgamo, L.; Huong, V.T.Q.; Monath, T.P.; Digoutte, J.P. and Deubel, V. 91994). "Geographic distribution and evolution of yellow fever viruses based on direct sequencing of genomic DNA fragments", J. Gn. Virol. 75–417–423.
Lobigs, M.; Usha, R.; Nesterowicz, A.; Marschall, I.D.; Weir, R.C. and Dalgamo, L. 9199). "host cell selection of Murray valley encephalitis virus variants altered at an RGD sequence in the envelope protein and in mouse neurovirulence". Virology. 176:587–595.
Sumiyoshi, H.; Hoke, C.H. and Trent, D.W. 91992). "Infectious Japanese encephalitis virus RNA can be synthesized from in vitro–ligated cDNA templates". J. Virol. 66:54255431.
Sumiyoshi, H.; Tignor, G.H., and Shope, R.E. (1995). "Characterization of a highly attenuated Japanese encephalitis virus generated from molecularly coned cDNA". J. Infect. Dis. 171–1144–1151.
Holland, J.; spindler, K.; Horodyski, H.; Grabau, e.; Nichol, S. and VandePol, S. (1982), "Rapid eveolution of RNA genomes". Science. 215:1577–1585.
Racaniello, V.R.; and Baltimore, d. (1981)I. "Cloned Poliovirus complementary DNA is infectious in mammalian cells". Science. 214:916–919.
Melton, D.A.; Krieg, P.A.; Rabagliati, M.R.; Maniatis, T.; Zinn, K. and Green, M.R. 91984). Efficient in vitro synthesis of biologically active RNA and RNA hybridizatrion probes from plasmids containing a bacteriophage SP6 promoter. Nucl. Acids. Res. 12:7035–2056.
Lai, C.J.; Zhao, B.; Hori, H. and Bray, M. (1991). "Infectious RNA transcribed from stably cloned full–length cDNA of dengue type 4 virus". Proc. Natl. Acad. Sci. USA 88:5139–5143.

(List continued on next page.)

Primary Examiner—Donna C. Wortman
(74) Attorney, Agent, or Firm—Nixon & Vanderhye, P.C.

(57) ABSTRACT

The present invention is related to a vaccine composition for humans against YF infections consisting essencially of a recombinant YF virus, YFiv5.2/DD, which is regenerated from YF infectious cDNA. There is provided new plasmids, pYF 5'3' IV/G1/2 and pYFM 5.2/T3/27, which together, have the complete sequence of said YF infectious cDNA. The method for producing recombinant YF virus and the Original, Primary and Secondary Seed Lots are other embodiments of the present invention.

15 Claims, 15 Drawing Sheets

OTHER PUBLICATIONS

Rice, C.M.; Grakoui, A.; Galler, R. and Chambers, T. (1989). "Transcription of infectious yelow fever RNA from full-length cDNA templates produced by in vitro ligation". The New Biologist. 1:285–296.

Marchevsky, R.S.; Mariano, J.; Ferreira, V.S.; Almeida, E.; Cerqueira, J.J.; Carvalho, R.; Pissumo, J.W., Travassos da Rosa, A.P.A.A Simoes, M.C.; Santos, C.N.D.; Ferreira, I.I.; Mulyaert, I.R.; Mann, G.F.; Rice, C.M. and Galler, R. 91995). "Phenotypic analysis of y ellow fever virus derived from complementary DNA". Am. J. Trop. Med. Hyg. 52(1):75–80.

Schoub, B.D.; Dommann, C.J.; Johnson, S.; Downie, C. and Patel, P.L. (1990). "Encephalitis in a 13–year old boy following 17D YF vaccine". J. Infection 21:105–106.

Merlo, C., Steffen, R.; Landis, T., Tsai, T. and Karabatsos, N. 91993). "Possible association of encephalitis and a 17D YF vaccination in a 29–year old traveller". Vaccine. 11:691.

Fox, J.P.; Lennette, E.H.; Manso, c. and Souza Aguiar, J.r. 91942). Encephalitis in man following vaccination with yellow fever 17d virus. Am. J.Hyg,. 36:17–142.

Fox, J.P.; and Penna, H.A. 91943). Behavior of 17D yellow fever virus in Rhesus monkeys. Relation to substrain, dose and neural of extraneural inoculation.: Am.J. Hyg. 38:52–172.

Post, P.R.; Duare dos Santos, C.N.; Carvalho, R.; Cruz, A.C.R.; Rice, c.M. and Galler, R. (1992). "Heterogeneity in envelope protein sequence and N–linked glycosylation among yellow fever vaccine strains". Virology. 188:160–167.

Konarska, M.M.; Padgett, R.A., Sharp, P.A. 91984). "Recognition of cap structure in splicing in vitro of mRNA precursors". Cell. 38:731–736.

Rice, C.M.; Lenches, E.M.; Eddy, S.r.; Shin, S.J.; sheets, R.L. and Strauss, J.H. 91985). "Nucleotide sequence of yellow fever virus: implications for flavivirus gene expression and evolution". Science. 229–726–633.

* cited by examiner

FIG. 6A

```
   1 AGTAAATCCT GTGTGCTAAT TGAGGTGCAT TGGTCTGCAA ATCGAGTTGC
  51 TAGGCAATAA ACACATTTGG ATTAATTTTA ATCGTTCGTT GAGCGATTAG
 101 CAGAGAACTG ACCAGAACAT GTCTGGTCGT AAAGCTCAGG GAAAAACCCT
 151 GGGCGTCAAT ATGGTACGAC GAGGAGTTCG CTCCTTGTCA AACAAAATAA
 201 AACAAAAAAC AAAACAAATT GGAAACAGAC CTGGACCTTC AAGAGGTGTT
 251 CAAGGATTTA TCTTTTTCTT TTTGTTCAAC ATTTTGACTG GAAAAAAGAT
 301 CACAGCCCAC CTAAAGAGGT TGTGGAAAAT GCTGGACCCA AGACAAGGCT
 351 TGGCTGTTCT AAGGAAAGTC AAGAGAGTGG TGGCCAGTTT GATGAGAGGA
 401 TTGTCCTCAA GGAAACGCCG TTCCCATGAT GTTCTGACTG TGCAATTCCT
 451 AATTTTGGGA ATGCTGTTGA TGACGGGTGG AGTGACCTTG GTGCGGAAAA
 501 ACAGATGGTT GCTCCTAAAT GTGACATCTG AGGACCTCGG GAAAACATTC
 551 TCTGTGGGCA CAGGCAACTG CACAACAAAC ATTTTGGAAG CCAAGTACTG
 601 GTGCCCAGAC TCAATGGAAT ACAACTGTCC AATCTCAGT CCAAGAGAGG
 651 AGCCAGATGA CATTGATTGC TGGTGCTATG GGGTGGAAAA CGTTAGAGTC
 701 GCATATGGTA AGTGTGACTC AGCAGGCAGG TCTAGGAGGT CAAGAAGGGC
 751 CATTGACTTG CCTACGCATG AAAACCATGG TTTGAAGACC CGGCAAGAAA
 801 AATGGATGAC TGGAAGAATG GGTGAAAGGC AACTCCAAAA GATTGAGAGA
 851 TGGTTCGTGA GGAACCCCTT TTTTGCAGTG ACGGCTCTGA CCATTGCCTA
 901 CCTTGTGGGA AGCAACATGA CGCAACGAGT CGTGATTGCC CTACTGGTCT
 951 TGGCTGTTGG TCCGGCCTAC TCAGCTCACT GCATTGGAAT TACTGACAGG
1001 GATTTCATTG AGGGGGTGCA TGGAGGAACT TGGGTTTCAG CTACCCTGGA
1051 GCAAGACAAG TGTGTCACTG TTATGGCCCC TGACAAGCCT TCATTGGACA
1101 TCTCACTAGA GACAGTAGCC ATTGATAGAC CTGCTGAGGC GAGGAAAGTG
1151 TGTTACAATG CAGTTCTCAC TCATGTGAAG ATTAATGACA GTGCCCCAG
1201 CACTGGAGAG GCCCACCTAG CTGAAGAGAA CGAAGGGGAC AATGCGTGCA
1251 AGCGCACTTA TTCTGATAGA GGCTGGGGCA ATGGCTGTGG CCTATTTGGG
1301 AAAGGGAGCA TTGTGGCATG CGCCAAATTC ACTTGTGCCA AATCCATGAG
1351 TTTGTTTGAG GTTGATCAGA CCAAAATTCA GTATGTCATC AGAGCACAAT
1401 TGCATGTAGG GGCCAAGCAG GAAAATTGGA ATACCAGCAT TAAGACTCTC
```

FIG. 6B

```
1451  AAGTTTGATG CCCTGTCAGG CTCCCAGGAA GTCGAGTTCA TTGGGTATGG
1501  AAAAGCTACA CTGGAATGCC AGGTGCAAAC TGCGGTGGAC TTTGGTAACA
1551  GTTACATCGC TGAGATGGAA ACAGAGAGCT GGATAGTGGA CAGACAGTGG
1601  GCCCAGGACT TGACCCTGCC ATGGCAGAGT GGAAGTGGCG GGGTGTGGAG
1651  AGAGATGCAT CATCTTGTCG AATTTGAACC TCCGCATGCC GCCACTATCA
1701  GAGTACTGGC CCTGGGAAAC CAGGAAGGCT CCTTGAAAAC AGCTCTTACT
1751  GGCGCAATGA GGGTTACAAA GGACACAAAT GACAACAACC TTTACAAACT
1801  ACATGGTGGA CATGTTTCTT GCAGAGTGAA ATTGTCAGCT TGACACTCA
1851  AGGGGACATC CTACAAAATA TGCACTGACA AAATGTTTTT TGTCAAGAAC
1901  CCAACTGACA CTGGCCATGG CACTGTTGTG ATGCAGGTGA AAGTGCCAAA
1951  AGGAGCCCCC TGCAGGATTC CAGTGATAGT AGCTGATGAT CTTACAGCGG
2001  CAATCAATAA AGGCATTTTG GTTACAGTTA ACCCCATCGC CTCAACCAAT
2051  GATGATGAAG TGCTGATTGA GGTGAACCCA CCTTTTGGAG ACAGCTACAT
2101  TATCGTTGGG AGAGGAGATT CACGTCTCAC TTACCAGTGG CACAAAGAGG
2151  GAAGCTCAAT AGGAAAGTTG TTCACTCAGA CCATGAAAGG CGTGGAACGC
2201  CTGGCCGTCA TGGGAGACGT CGCCTGGGAT TCAGCTCCG CTGGAGGGTT
2251  CTTCACTTCG GTTGGGAAAG GAATTCATAC GGTGTTTGGC TCTGCCTTTC
2301  AGGGGCTATT TGGCGGCTTG AACTGGATAA CAAAGGTCAT CATGGGGGCG
2351  GTACTCATAT GGGTTGGCAT CAACACAAGA AACATGACAA TGTCCATGAG
2401  CATGATCTTG GTAGGAGTGA TCATGATGTT TTTGTCTCTA GGAGTTGGGG
2451  CGGATCAAGG ATGCGCCATC AACTTTGGCA AGAGAGAGCT CAAGTGCGGA
2501  GATGGTATCT TCATATTTAG AGACTCTGAT GACTGGCTGA ACAAGTACTC
2551  ATACTATCCA GAAGATCCTG TGAAGCTTGC ATCAATAGTG AAAGCCTCTT
2601  TCGAAGAAGG GAAGTGTGGC CTAAATTCAG TTGACTCCCT TGAGCATGAG
2651  ATGTGGAGAA GCAGGGCAGA TGAGATTAAT ACCATTTTTG AGGAAAACGA
2701  GGTGGACATT TCTGTTGTCG TGCAGGATCC AAAGAATGTT TACCAGAGAG
2751  GAACTCATCC ATTTTCCAGA ATTCGGGATG GTCTGCAGTA TGGTTGGAAG
2801  ACTTGGGGTA AGAACCTTGT GTTCTCCCCA GGGAGGAAGA ATGGAAGCTT
```

FIG. 6C

```
2851 CATCATAGAT GGAAAGTCCA GGAAAGAATG CCCGTTTTCA AACCGGGTCT
2901 GGAATTCTTT CCAGATAGAG GAGTTTGGGA CGGGAGTGTT CACCACACGC
2951 GTGTACATGG ACGCAGTCTT TGAATACACC ATAGACTGCG ATGGATCTAT
3001 CTTGGGTGCA GCGGTGAACG GAAAAAAGAG TGCCCATGGC TCTCCAACAT
3051 TTTGGATGGG AAGTCATGAA GTAAATGGGA CATGGATGAT CCACACCTTG
3101 GAGGCATTAG ATTACAAGGA GTGTGAGTGG CCACTGACAC ATACGATTGG
3151 AACATCAGTT GAAGAGAGTG AAATGTTCAT GCCGAGATCA ATCGGAGGCC
3201 CAGTTAGCTC TCACAATCAT ATCCCTGGAT ACAAGGTTCA GACGAACGGA
3251 CCTTGGATGC AGGTACCACT AGAAGTGAAG AGAGAAGCTT GCCCAGGGAC
3301 TAGCGTGATC ATTGATGGCA ACTGTGATGG ACGGGGAAAA TCAACCAGAT
3351 CCACCACGGA TAGCGGGAAA GTTATTCCTG AATGGTGTTG CCGCTCCTGC
3401 ACAATGCCGC CTGTGAGCTT CCATGGTAGT GATGGGTGTT GGTATCCCAT
3451 GGAAATTAGG CCAAGGAAAA CGCATGAAAG CCATCTGGTG CGCTCCTGGG
3501 TTACAGCTGG AGAAATACAT GCTGTCCCTT TTGGTTTGGT GAGCATGATG
3551 ATAGCAATGG AAGTGGTCCT AAGGAAAAGA CAGGGACCAA AGCAAATGTT
3601 GGTTGGAGGA GTAGTGCTCT TGGGAGCAAT GCTGGTCGGG CAAGTAACTC
3651 TCCTTGATTT GCTGAAACTC ACAGTGGCTG TGGGATTGCA TTTCCATGAG
3701 ATGAACAATG GAGGAGACGC CATGTATATG GCGTTGATTG CTGCCTTTTC
3751 AATCAGACCA GGGCTGCTCA TCGGCTTTGG GCTCAGGACC CTATGGAGCC
3801 CTCGGGAACG CCTTGTGCTG ACCCTAGGAG CAGCCATGGT GGAGATTGCC
3851 TTGGGTGGCG TGATGGGCGG CCTGTGGAAG TATCTAAATG CAGTTTCTCT
3901 CTGCATCCTG ACAATAAATG CTGTTGCTTC TAGGAAAGCA TCAAATACCA
3951 TCTTGCCCCT CATGGCTCTG TTGACACCTG TCACTATGGC TGAGGTGAGA
4001 CTTGCCGCAA TGTTCTTTTG TGCCGTGGTT ATCATAGGGG TCCTTCACCA
4051 GAATTTCAAG GACACCTCCA TGCAGAAGAC TATACCTCTG GTGGCCCTCA
4101 CACTCACATC TTACCTGGGC TTGACACAAC CTTTTTTGGG CCTGTGTGCA
4151 TTTCTGGCAA CCCGCATATT TGGGCGAAGG AGTATCCCAG TGAATGAGGC
4201 ACTCGCAGCA GCTGGTCTAG TGGGAGTGCT GGCAGGACTG GCTTTTCAGG
```

FIG. 6D

```
4251 AGATGGAGAA CTTCCTTGGT CCGATTGCAG TTGGAGGACT CCTGATGATG
4301 CTGGTTAGCG TGGCTGGGAG GGTGGATGGG CTAGAGCTCA AGAAGCTTGG
4351 TGAAGTTTCA TGGGAAGAGG AGGCGGAGAT CAGCGGGAGT TCCGCCCGCT
4401 ATGATGTGGC ACTCAGTGAA CAAGGGGAGT TCAAGCTGCT TTCTGAAGAG
4451 AAAGTGCCAT GGGACCAGGT TGTGATGACC TCGCTGGCCT TGGTTGGGGC
4501 TGCCCTCCAT CCATTTGCTC TTCTGCTGGT CCTTGCTGGG TGGCTGTTTC
4551 ATGTCAGGGG AGCTAGGAGA AGTGGGGATG TCTTGTGGGA TATTCCCACT
4601 CCTAAGATCA TCGAGGAATG TGAACATCTG GAGGATGGGA TTTATGGCAT
4651 ATTCCAGTCA ACCTTCTTGG GGGCCTCCCA GCGAGGAGTG GGAGTGGCAC
4701 AGGGAGGGGT GTTCCACACA ATGTGGCATG TCACAAGAGG AGCTTTCCTT
4751 GTCAGGAATG GCAAGAAGTT GATTCCATCT TGGGCTTCAG TAAAGGAAGA
4801 CCTTGTCGCC TATGGTGGCT CATGGAAGTT GGAAGGCAGA TGGGATGGAG
4851 AGGAAGAGGT CCAGTTGATC GCGGCTGTTC CAGGAAAGAA CGTGGTCAAC
4901 GTCCAGACAA AACCGAGCTT GTTCAAAGTG AGGAATGGGG GAGAAATCGG
4951 GGCTGTCGCT CTTGACTATC CGAGTGGCAC TTCAGGATCT CCTATTGTTA
5001 ACAGGAACGG AGAGGTGATT GGGCTGTACG GCAATGGCAT CCTTGTCGGT
5051 GACAACTCCT TCGTGTCCGC CATATCCCAG ACTGAGGTGA AGGAAGAAGG
5101 AAAGGAGGAG CTCCAAGAGA TCCCGACAAT GCTAAAGAAA GGAATGACAA
5151 CTGTCCTTGA TTTTCATCCT GGAGCTGGGA AGACAAGACG TTTCCTCCCA
5201 CAGATCTTGG CCGAGTGCGC ACGGAGACGC TTGCGCACTC TTGTGTTGGC
5251 CCCCACCAGG GTTGTTCTTT CTGAAATGAA GGAGGCTTTT CACGGCCTGG
5301 ACGTGAAATT CCACACACAG GCTTTTTCCG CTCACGGCAG CGGGAGAGAA
5351 GTCATTGATG CCATGTGCCA TGCCACCCTA ACTTACAGGA TGTTGGAACC
5401 AACTAGGGTT GTTAACTGGG AAGTGATCAT TATGGATGAA GCCCATTTTT
5451 TGGATCCAGC TAGCATAGCC GCTAGAGGTT GGGCAGCGCA CAGAGCTAGG
5501 GCAAATGAAA GTGCAACAAT CTTGATGACA GCCACACCGC CTGGGACTAG
5551 TGATGAATTT CCACATTCAA ATGGTGAAAT AGAAGATGTT CAAACGGACA
5601 TACCCAGTGA GCCCTGGAAC ACAGGGCATG ACTGGATCCT AGCTGACAAA
```

FIG. 6E

```
5651 AGGCCCACGG CATGGTTCCT TCCATCCATC AGAGCTGCAA ATGTCATGGC
5701 TGCCTCTTTG CGTAAGGCTG GAAAGAGTGT GGTGGTCCTG AACAGGAAAA
5751 CCTTTGAGAG AGAATACCCC ACGATAAAGC AGAAGAAACC TGACTTTATA
5801 TTGGCCACTG ACATAGCTGA AATGGGAGCC AACCTTTGCG TGGAGCGAGT
5851 GCTGGATTGC AGGACGGCTT TTAAGCCTGT GCTTGTGGAT GAAGGGAGGA
5901 AGGTGGCAAT AAAAGGGCCA CTTCGTATCT CCGCATCCTC TGCTGCTCAA
5951 AGGAGGGGGC GCATTGGGAG AAATCCCAAC AGAGATGGAG ACTCATACTA
6001 CTATTCTGAG CCTACAAGTG AAAATAATGC CCACCACGTC TGCTGGTTGG
6051 AGGCCTCAAT GCTCTTGGAC AACATGGAGG TGAGGGGTGG AATGGTCGCC
6101 CCACTCTATG GCGTTGAAGG AACTAAAACA CCAGTTTCCC CTGGTGAAAT
6151 GAGACTGAGG GATGACCAGA GGAAAGTCTT CAGAGAACTA GTGAGGAATT
6201 GTGACCTGCC CGTTTGGCTT TCGTGGCAAG TGGCCAAGGC TGGTTTGAAG
6251 ACGAATGATC GTAAGTGGTG TTTTGAAGGC CCTGAGGAAC ATGAGATCTT
6301 GAATGACAGC GGTGAAACAG TGAAGTGCAG GGCTCCTGGA GGAGCAAAGA
6351 AGCCTCTGCG CCCAAGGTGG TGTGATGAAA GGGTGTCATC TGACCAGAGT
6401 GCGCTGTCTG AATTTATTAA GTTTGCTGAA GGTAGGAGGG GAGCTGCTGA
6451 AGTGCTAGTT GTGCTGAGTG AACTCCCTGA TTTCCTGGCT AAAAAAGGTG
6501 GAGAGGCAAT GGATACCATC AGTGTGTTTC TCCACTCTGA GGAAGGCTCT
6551 AGGGCTTACC GCAATGCACT ATCAATGATG CCTGAGGCAA TGACAATAGT
6601 CATGCTGTTT ATACTGGCTG GACTACTGAC ATCGGGAATG GTCATCTTTT
6651 TCATGTCTCC CAAAGGCATC AGTAGAATGT CTATGGCGAT GGGCACAATG
6701 GCCGGCTGTG GATATCTCAT GTTCCTTGGA GGCGTCAAAC CCACTCACAT
6751 CTCCTATATC ATGCTCATAT TCTTTGTCCT GATGGTGGTT GTGATCCCCG
6801 AGCCAGGGCA ACAAAGGTCC ATCCAAGACA ACCAAGTGGC ATACCTCATT
6851 ATTGGCATCC TGACGCTGGT TCAGCGGTG GCAGCCAACG AGCTAGGCAT
6901 GCTGGAGAAA ACCAAAGAGG ACCTCTTTGG GAAGAAGAAC TTAATTCCAT
6951 CTAGTGCTTC ACCCTGGAGT TGGCCGGATC TTGACCTGAA GCCAGGAGCT
7001 GCCTGGACAG TGTACGTTGG CATTGTTACA ATGCTCTCTC CAATGTTGCA
```

FIG. 6F

```
7051 CCACTGGATC AAAGTCGAAT ATGGCAACCT GTCTCTGTCT GGAATAGCCC
7101 AGTCAGCCTC AGTCCTTTCT TTCATGGACA AGGGGATACC ATTCATGAAG
7151 ATGAATATCT CGGTCATAAT GCTGCTGGTC AGTGGCTGGA ATTCAATAAC
7201 AGTGATGCCT CTGCTCTGTG GCATAGGGTG CGCCATGCTC CACTGGTCTC
7251 TCATTTTACC TGGAATCAAA GCGCAGCAGT CAAAGCTTGC ACAGAGAAGG
7301 GTGTTCCATG GCGTTGCCAA GAACCCTGTG GTTGATGGGA ATCCAACAGT
7351 TGACATTGAG GAAGCTCCTG AAATGCCTGC CCTTTATGAG AAGAAACTGG
7401 CTCTATATCT CCTTCTTGCT CTCAGCCTAG CTTCTGTTGC CATGTGCAGA
7451 ACGCCCTTTT CATTGGCTGA AGGCATTGTC CTAGCATCAG CTGCCTTAGG
7501 GCCGCTCATA GAGGGAAACA CCAGCCTTCT TTGGAATGGA CCCATGGCTG
7551 TCTCCATGAC AGGAGTCATG AGGGGGAATC ACTATGCTTT TGTGGGAGTC
7601 ATGTACAATC TATGGAAGAT GAAAACTGGA CGCCGGGGGA GCGCGAATGG
7651 AAAAACTTTG GGTGAAGTCT GGAAGAGGGA ACTGAATCTG TTGGACAAGC
7701 GACAGTTTGA GTTGTATAAA AGGACCGACA TTGTGGAGGT GGATCGTGAT
7751 ACGGCACGCA GGCATTTGGC CGAAGGGAAG GTGGACACCG GGGTGGCGGT
7801 CTCCAGGGGG ACCGCAAAGT TAAGGTGGTT CCATGAGCGT GGCTATGTCA
7851 AGCTGGAAGG TAGGGTGATT GACCTGGGGT GTGGCCGCGG AGGCTGGTGT
7901 TACTACGCTG CTGCGCAAAA GGAAGTGAGT GGGGTCAAAG GATTTACTCT
7951 TGGAAGAGAC GGCCATGAGA AACCCATGAA TGTGCAAAGT CTGGGATGGA
8001 ACATCATCAC CTTCAAGGAC AAAACTGATA TCCACCGCCT AGAACCAGTG
8051 AAATGTGACA CCCTTTTGTG TGACATTGGA GAGTCATCAT CGTCATCGGT
8101 CACAGAGGGG GAAAGGACCG TGAGAGTTCT TGATACTGTA GAAAAATGGC
8151 TGGCTTGTGG GGTTGACAAC TTCTGTGTGA AGGTGTTAGC TCCATACATG
8201 CCAGATGTTC TCGAGAAACT GGAATTGCTC CAAAGGAGGT TGGCGGAAC
8251 AGTGATCAGG AACCCTCTCT CCAGGAATTC CACTCATGAA ATGTACTACG
8301 TGTCTGGAGC CCGCAGCAAT GTCACATTTA CTGTGAACCA AACATCCCGC
8351 CTCCTGATGA GGAGAATGAG GCGTCCAACT GGAAAAGTGA CCCTGGAGGC
8401 TGACGTCATC CTCCCAATTG GGACACGCAG TGTTGAGACA GACAAGGGAC
```

FIG. 6G

```
8451 CCCTGGACAA AGAGGCCATA GAAGAAAGGG TTGAGAGGAT AAAATCTGAG
8501 TACATGACCT CTTGGTTTTA TGACAATGAC AACCCCTACA GGACCTGGCA
8551 CTACTGTGGC TCCTATGTCA CAAAAACCTC AGGAAGTGCG GCGAGCATGG
8601 TAAATGGTGT TATTAAAATT CTGACATATC CATGGGACAG GATAGAGGAG
8651 GTCACCAGAA TGGCAATGAC TGACACAACC CCTTTTGGAC AGCAAAGAGT
8701 GTTTAAAGAA AAAGTTGACA CCAGAGCAAA GGATCCACCA GCGGGAACTA
8751 GGAAGATCAT GAAAGTTGTC AACAGGTGGC TGTTCCGCCA CCTGGCCAGA
8801 GAAAAGAGCC CCAGACTGTG CACAAAGGAA GAATTTATTG CAAAAGTCCG
8851 AAGTCATGCA GCCATTGGAG CTTACCTGGA AGAACAAGAA CAGTGGAAGA
8901 CTGCCAATGA GGCTGTCCAA GACCCAAAGT TCTGGGAACT GGTGGATGAA
8951 GAAAGGAAGC TGCACCAACA AGGCAGGTGT CGGACTTGTG TGTACAACAT
9001 GATGGGGAAA AGAGAGAAGA AGCTGTCAGA GTTTGGGAAA GCAAAGGGAA
9051 GCCGTGCCAT ATGGTATATG TGGCTGGGAG CGCGGTATCT TGAGTTTGAG
9101 GCCCTGGGAT TCCTGAATGA GGACCATTGG GCTTCCAGGG AAAACTCAGG
9151 AGGAGGAGTG GAAGGCATTG GCTTACAATA CCTAGGATAT GTGATCAGAG
9201 ACCTGGCTGC AATGGATGGT GGTGGATTCT ACGCGGATGA CACCGCTGGA
9251 TGGGACACGC GCATCACAGA GGCAGACCTT GATGATGAAC AGGAGATCTT
9301 GAACTACATG AGCCCACATC ACAAAAAACT GGCACAAGCA GTGATGGAAA
9351 TGACATACAA GAACAAAGTG GTGAAAGTGT TGAGACCAGC CCCAGGAGGG
9401 AAAGCCTACA TGGATGTCAT AAGTCGACGA GACCAGAGAG GATCCGGGCA
9451 GGTAGTGACT TATGCTCTGA ACACCATCAC CAACTTGAAA GTCCAATTGA
9501 TCAGAATGGC AGAAGCAGAG ATGGTGATAC ATCACCAACA TGTTCAAGAT
9551 TGTGATGAAT CAGTTCTGAC CAGGCTGGAG GCATGGCTCA CTGAGCACGG
9601 ATGTAACAGA CTGAAGAGGA TGGCGGTGAG TGGAGACGAC TGTGTGGTCC
9651 GGCCCATCGA TGACAGGTTC GGCCTGGCCC TGTCCCATCT CAACGCCATG
9701 TCCAAGGTTA GAAAGGACAT ATCTGAATGG CAGCCATCAA AGGGTGGAA
9751 TGATTGGGAG AATGTGCCCT TCTGTTCCCA CCACTTCCAT GAACTACAGC
9801 TGAAGGATGG CAGGAGGATT GTGGTGCCTT GCCGAGAACA GGACGAGCTC
```

FIG. 6H

9851 ATTGGGAGAG GAAGGGTGTC TCCAGGAAAC GGCTGGATGA TCAAGGAAAC

9901 AGCTTGCCTC AGCAAAGCCT ATGCCAACAT GTGGTCACTG ATGTATTTTC

9951 ACAAAAGGGA CATGAGGCTA CTGTCATTGG CTGTTTCCTC AGCTGTTCCC

10001 ACCTCATGGG TTCCACAAGG ACGCACAACA TGGTCGATTC ATGGGAAAGG

10051 GGAGTGGATG ACCACGGAAG ACATGCTTGA GGTGTGGAAC AGAGTATGGA

10101 TAACCAACAA CCCACACATG CAGGACAAGA CAATGGTGAA AAAATGGAGA

10151 GATGTCCCTT ATCTAACCAA GAGACAAGAC AAGCTGTGCG GATCACTGAT

10201 TGGAATGACC AATAGGGCCA CCTGGGCCTC CCACATCCAT TTAGTCATCC

10251 ATCGTATCCG AACGCTGATT GGACAGGAGA AATACACTGA CTACCTAACA

10301 GTCATGGACA GGTATTCTGT GGATGCTGAC CTGCAACTGG GTGAGCTTAT

10351 CTGAAACACC ATCTAACAGG AATAACCGGG ATACAAACCA CGGGTGGAGA

10401 ACCGGACTCC CCACAACCTG AAACCGGGAT ATAAACCACG GCTGGAGAAC

10451 CGGACTCCGC ACTTAAAATG AAACAGAAAC CGGGATAAAA ACTACGGATG

10501 GAGAACCGGA CTCCACACAT TGAGACAGAA GAAGTTGTCA GCCCAGAACC

10551 CCACACGAGT TTTGCCACTG CTAAGCTGTG AGGCAGTGCA GGCTGGGACA

10601 GCCGACCTCC AGGTTGCGAA AAACCTGGTT TCTGGGACCT CCCACCCCAG

10651 AGTAAAAAGA ACGGAGCCTC CGCTACCACC CTCCCACGTG GTGGTAGAAA

10701 GACGGGGTCT AGAGGTTAGA GAAGACCCTC CAGGGAACAA ATAGTGGGAC

10751 CATATTGACG CCAGGGAAAG ACCGGAGTGG TTCTCTGCTT TTCCTCCAGA

10801 GGTCTGTGAG CACAGTTTGC TCAAGAATAA GCAGACCTTT GGATGACAAA

10851 CACAAAACCA CT

FIG. 7

VACCINES AGAINST INFECTIONS CAUSED BY YF VIRUS; YF INFECTIOUS CDNA, METHOD FOR PRODUCING A RECOMBINANT YF VIRUS FROM THE YF INFECTIOUS CDNA AND PLASMIDS TO ASSEMBLE THE YF INFECTIOUS CDNA

This is a division of application Ser. No. 09/058,411, filed Apr. 10, 1998 now U.S. Pat. No. 6,171,854.

The present invention relates to a vaccine against infections caused by YF virus and its preparation by regenerating YF 17D virus from the correspondent complementary DNA (cDNA) which is present in the new plasmids pYF 5'3' IV/G1/2 and pYFM 5.2/T3/27.

BACKGROUND OF THE INVENTION

The Flavivirus genus consists of 70 serologically cross-reactive, closely related human or veterinary pathogens causing many serious illnesses, which includes dengue fever, Japanese encephalitis (JE), tick-borne encephalitis (TBE) and yellow fever (YF). The Flaviviruses are spherical with 40–60 nm in diameter with an icosahedral capsid which contains a single positive-stranded RNA molecule.

YF virus is the prototype virus of the family of the Flaviviruses with a RNA genome of 10,862 nucleotides (nt), having a 5' CAP structure (118 nt) and a nonpolyadenylated 3' end (511 nt). The complete nucleotide sequence, of its RNA genome was determined by Rice, C. M. et al (1985).

The single RNA is also the viral message and its translation in the infected cell results in the synthesis of a polyprotein precursor of 3,411 amino acids which is cleaved by proteolytic processing to generate 10 virus-specific polypeptides. From the 5' terminus, the order of the encoded proteins is: C; prM/M; E; NS1; NS2A; NS2B; NS3; NS4A; NS4B and NS5. The first 3 proteins constitute the structural proteins, i.e., they form the virus together with the packaged RNA molecule. The remainder of the genome codes for the nonstructural proteins (NS) numbered from 1 through 5, according the order of their synthesis.

The C protein, named capsid, has a molecular weight ranging from 12 to 14 kDa (12–14 kilodaltons); the membrane protein, M has a molecular weight of 8 kDa, and its precursor (prM) 18–22 kDa; the envelope protein, E, has 52–54 kDa, being all of them encoded in the first quarter of their genome.

Three of the nonstructural proteins are large and have highly conserved sequences among the flaviviruses, namely, NS1 has a molecular weight ranging from 38 to 41 kDa; NS3 has 68–70 kDa and NS5, 100–103 kDa. No role has yet been assigned to NS1 but NS3 has been shown to be bifunctional having a protease activity needed for the processing of the polyprotein, and the other is a nucleotide triphosphatase/helicase activity which is associated with viral RNA replication. NS5, the largest and most conserved protein, contains several sequence motifs which are characteristic of viral RNA polymerases. The 4 small proteins, namely NS2A, NS2B, NS4A and NS4B, are poorly conserved in their amino acid sequences but not in their pattern of multiple hydrophobic stretches. NS2A has been shown to be required for proper processing of NS1 whereas NS2B has been shown to be associated with the protease activity of NS3.

Two strains of yellow fever virus (YF), isolated in 1927, gave rise to the vaccines to be used for human immunization. One, the Asibi strain, was isolated from a young african named Asibi by passage in Rhesus monkey (Macaca mulatta), and the other, the French Viscerotropic Virus (FVV), from a patient in Senegal.

In 1935, the Asibi strain was adapted to growth in mouse embryonic tissue. After 17 passages, the virus, named 17D, was further cultivated until passage 58 in whole chicken embryonic tissue and thereafter, until passage 114, in denervated chicken embryonic tissue only. Theiler and Smith (Theiler, M. and Smith, H. H. (1937). "The effect of prolonged cultivation in vitro upon the pathogenicity of yellow fever virus". J. Exp. Med. 65:767–786) showed that, at this stage, there was a marked reduction in viral viscero and neurotropism when inoculated intracerebrally in monkeys. This virus was further subcultured until passages 227 and 229 and the resulting viruses, without human immune serum, were used to immunize 8 human volunteers with satisfactory results, as shown by the absence of adverse reactions and seroconversion to YF in 2 weeks. These passages yielded the parent 17D strain at passage level 180 (see FIG. 1), 17DD at passage 195, and the 17D-204 at passage 204. 17DD was further subcultured until passage 241 and underwent 43 additional passages in embryonated chicken eggs to yield the virus currently used for human vaccination in some countries (passage 284). The 17D-204 was further subcultured to produce Colombia 88 strain which, upon passage in embryonated chicken eggs, gave rise to different vaccine seed lots currently in use in France (I. Pasteur, at passage 235) and in the United States (Connaught, at passage 234). The 17D-213 strain was derived from 17D-204 when the primary seed lot (S1 112–69) from the Federal Republic of Germany (FRG 83–66) was used by the World Health Organization (WHO) to produce an avian leukosis virus-free 17D seed (S1 213/77) at passage 237.

In the late 1930's and early 1940's, mass vaccination was conducted in Brazil with the use of several substrains of 17D virus (Table I). These substrains differed in their passage history and they overlapped with regard to time of their use for inocula and/or vaccine production. The substitution of each one by the next was according to the experience gained during vaccine production, quality control and human vaccination in which the appearance of symptomatology led to the discontinuation of a given strain.

Each of these 17D-204 strains (C-204; F-204) was plaque purified in different cell lines, the virus finally amplified in SW13 cells and used for cDNA cloning and sequence analyses (Rice, C. M.; Lenches, E.; Eddy, S. R.; Shin, S. J.; Sheets, R. L. and Strauss, J. H. (1985). "Nucleotide sequence of yellow fever virus: implications for flavivirus gene expression and evolution". Science. 229: 726–733; Despres, P.; Cahour, A.; Dupuy, A.; Deubel, V.; Bouloy, M.; Digoutte, J. P.; Girard, M. (1987). "High genetic stability of the coding region for the structural proteins of yellow fever strain 17D". J. Gen. Virol. 68: 2245–2247).

The 17D-213 at passage 239 was tested for monkey neurovirulence (R. S. Marchevsky, personal communication, see Duarte dos Santos et al, 1995) and was the subject of sequence analysis together with 17DD (at passage 284) and comparison to previously published nucleotide sequences of other YF virus strains (Duarte dos Santos et al, 1995) (Asibi: Hahn, C. S.; Dalrymple, J. M.; Strauss, J. H. and Rice, C. M. (1987). "Comparison of the virulent Asibi strain of yellow fever virus with the 17D vaccine strain derived from it". Proc. Natl. Acad. Sci. USA. 84: 2029–2033; 17D-204 strain, C-204: Rice. C. M.; Lenches, E. M.; Eddy, S. R.; Shin, S. J.; Sheets, R. L. and Strauss, J. H. (1985). "Nucleotide sequence of yellow fever virus: implications for flavivirus gene expression and evolution".

Science. 229: 726–733; F-204: Despres, P.; Cahour, R.; Dupuy, A.; Deubel, V.; Bouloy, M.; Digoutte, J. P. and Girard, M. (1987). "High genetic stability of the coding region for the structural proteins of yellow fever virus strain 17D". J. Gen. Virol. 68: 2245–2247) (see FIG. 1).

A total of 67 nucleotide differences, corresponding to 31 amino acid changes, were originally noted between the Asibi and 17D-204 genomic sequences (see Hahn, C. S. et al, 1987). The comparison between the nucleotide sequences of 17DD and 17D-213 substrains (see Duarte dos Santos et al, 1995) and the nucleotide sequence of 17D-204 substrain (see Rice et al, 1985) showed that not all changes are common and thus not confirmed as being 17D-specific. Therefore, the 17D-substrain specific changes observed are very likely not related to attenuation but may reflect differences in behavior of these strains in monkey neurovirulence tests. In consequence, the number of changes likely to be associated with viral attenuation were reduced by 26%, i.e., to 48 nucleotide changes. From these 48 nucleotide sequence changes which are scattered along the genome, 26 are silent mutations and 22 led to amino acid substitutions. More important are the alterations noted in the E protein because it is the main target for humoral neutralizing response, i.e., it is the protein where hemagglutination and neutralization epitopes are located, and it mediates cell receptor recognition and cell penetration, therefore targeting the virus to specific cells. Importantly, E protein accumulate the highest ratio of nonconservative to conservative amino acid changes. Altogether, eleven nucleotide substitutions were observed in the E protein gene leading to 8 amino acid changes at positions 52, 170, 173, 200, 299, 305, 331 and 380 (respectively nucleotides 1127, 1482, 1491, 1572, 1870, 1887, 1965 and 2112 from the RNA 5' end).

Alterations at amino acids 52 and 200 are located in domain A of E protein (domain II in 3-D structure proposed for Flaviviruses E protein—Rey, F. A.; Heinz F. X.; Mandl, C.; Kunz, C and Harrison, S. C. (1995). "The envelope glycoprotein from tick-borne encephalitis virus at 2 Å resolution". Nature. 375: 291–298) which is conserved among Flaviviruses and contains cross-reactive epitopes as shown by Mandl, C. W. et al (Mandl, M. W.; Guirakhoo, F.; Holzmann, H.; Heinz, F. X. and Kunz, C. (1989). "Antigenic structure of the flavivirus envelope E protein at the molecular level using tick-borne encephalitis virus as a model". J. Virol. 63: 564–571). This domain II is highly crosslinked by disulphide bonds and undergoes low pH transition which is related to exposing a strictly conserved and hydrophobic stretch of amino acids which are supposed to be involved in the fusion of the viral envelope to the endosome membrane.

Alterations at amino acids 299, 305, 331 and 380 are located in the B domain (domain III in the 3-D structure—see Rey, F. A. et al). This domain was suggested to be involved in viral attachment to a cellular receptor and consequently being a major determinant both of host range and cell tropism and of virulence/attenuation. The 4 amino acid changes reported for YF are located on the distal face of domain III. This area has a loop which is a tight turn in tick-borne encephalitis virus but contains 4 additional residues in all mosquito-borne strains. Because viruses replicate in their vectors, this loop is likely to be a host range determinant. This enlarged loop contains an Arginine-Glycine-Aspartic Acid (Arg-Gly-Asp) sequence in all 3 YF 17D vaccine strains. This sequence motif is known to mediate a number of cell interactions including receptor binding and is absent not only in the parental virulent Asibi strain but also in other 22 strains of YF wild type virus (Lepiniec, L.; Dalgarno, L.; Huong, V. T. Q.; Monath, T. P.; Digoutte, J. P. and Deubel, V. (1994). "Geographic distribution and evolution of yellow fever viruses based on direct sequencing of genomic DNA fragments". J. Gen. Virol. 75: 417–423). Such a fact suggests that the mutation from Threonine (Thr) to Arginine (Arg), creating a Arg-Gly-Asp motif, is likely to be relevant for the attenuated phenotype of the YF 17D strain. Consistently, Lobigs et al (Lobigs, M.; Usha, R.; Nesterowicz, A.; Marschall, I. D.; Weir, R. C. and Dalgarno, L. (1990). "Host cell selection of Murray Valley encephalitis virus variants altered at an RGD sequence in the envelope protein and in mouse neurovirulence". Virology. 176: 587–595) identified a Arg-Gly-Asp sequence motif (at amino acid 390) which led to the loss of virulence of Murray Valley encephalitis virus for mice.

Alterations at amino acids 170 and 173 in domain C (domain I of the E protein in the 3-D structure) map very close to the position that a neutralization epitope was identified for tick-borne encephalitis (TBE) virus (see Mandl, C. W. et al) . A mutation at position 171 of TBE virus E protein was shown to affect the threshold of fusion-activating conformational change of this protein and the 2 changes observed for YF 17D virus may be related to same phenomenon. It is conceivable that a slower rate of fusion may delay the extent of virus production and thereby lead to a milder infection of the host. It is noteworthy that the recent development of infectious cDNA for Japanese encephalitis (JE) virus made by Sumiyoshi, H. et al (Sumiyoshi, H.; Hoke, C. H. and Trent, D. W. (1992). "Infectious Japanese encephalitis virus RNA can be synthesized from in vitro-ligated cDNA templates". J. Virol. 66: 5425–5431) allowed the identification of a mutation (Lys for Glu) at amino acid 136 of the E protein which resulted in the loss of neurovirulence for mice (see Sumiyoshi, H.; Tignor, G. H. and Shope, R. E. (1996). "Characterization of a highly attenuated Japanese encephalitis virus generated from molecularly cloned cDNA". J. Infect. Dis. 171: 1144–1151). This means that domain I is an important area which contains a critical determinant of JE virus virulence in contrast to most of the data obtained from the analyses of virulence for several other flaviviruses for which it is suggested that domain III would be the primary site for virulence/attenuation determinants. Nevertheless, such analyses of the E protein provides a framework for understanding several aspects of flavivirus biology and suggests that it should be possible to engineer viruses for the development of new live flavivirus vaccine.

The issue of virulence/attenuation is of special interest for vaccine development but conceivably viral attenuation can result from genetic modification in one or more viral functions. YF virus is the ideal system to study flavivirus virulence and attenuation because: (i) there is a virulent strain (Asibi) from which an extremely well characterized vaccine strain was derived (17D) and has been successfully used for human vaccination for over 50 years; (ii) there is an animal system which reflects human infection; (iii) the complete nucleotide sequences from both virulent and attenuated strains have been determined and (iv) cDNA clones from which infectious RNA can be synthesized are available. Holland, J. et al (Holland, J.; Spindler, K.; Horodyski, H.; Grabau, E.; Nichol, S. and VandePol, S. (1982). "Rapid evolution of RNA genomes". Science. 215: 1577–1585) described the fact that viral RNA genomes evolve rapidly. Therefore, a given viral population including YF vaccine viruses is likely to consist of a major type sequence population in which genetic variants can be detected. For YF 17D virus, this is easily seen when the virus is plagued on cultured cells under an semi-solid overlay in which plaques of different sizes are observed. Previous genomic variability analysis using oligonucleotide fingerprinting suggested a high degree of genetic similarity between vaccines produced worldwide with an estimated sequence homology of 98–100%. However, genetic changes were detected and may have occurred within 1–2 passages possibly due to the selection of virion subpopulations or to point mutations. It is unknown whether the outstanding vaccine properties of the YF 17D virus are due to the existence of genetic variants in the vaccine population. Anywise, the stabilization of the YF 17D genome as DNA not only will reduce the accumulation of mutations in the viral genome as seed lots are produced to replace the previous one but will also provide a much more homogeneous population in terms of nucleotide sequence and consequently in terms of phenotypic markers including attenuation for humans, thereby providing the necessary standardization of YF substrain use for vaccine production.

The capability to manipulate the genome of flaviviruses through infectious clone technology has opened new possibilities for vaccine development. This is so because virus can be recovered from complementary DNA by in vitro transcription and transfection of cultured cells with RNA, and these cDNAs corresponding to the complete viral genome allow introducing genetic modifications at any particular site of the viral genome. The pioneer study of Racaniello and Baltimore (Racaniello, V. R. and Baltimore, D. (1981). "Cloned poliovirus complementary DNA is infectious in mammalian cells". Science. 214: 916–919) first showed the feasibility to regenerate virus from cloned cDNA. In the patent U.S. Pat. No. 4,719,177, Racaniello and Baltimore described, in details, the production of RNA viral cDNA by reverse transcribing viral RNA and inserting the resulting cDNA molecule into a recombinant DNA vector. The process was particularly concerned to the production of poliovirus double-stranded complementary DNA (ds cDNA). They found out that the transfected full-length poliovirus cDNA was itself infectious.

In addition, with the development of in vitro transcription systems (see Melton, D. A.; Krieg, P. A.; Rabagliati, M. R.; Maniatis, T.; Zinn, K. and Green, M. R. (1984). "Efficient in vitro synthesis of biologically active RNA and RNA hybridization probes from plasmids containing a bacteriophage SP6 promoter". Nucl. Acids. Res. 12: 7035–7056), a much higher efficiency in the synthesis of full length viral RNA, as compared to cDNA transcription in the cell, became possible. Furthermore, the development of improved transfection methodologies such as cationic liposomes and electroporation increased the efficiency of RNA transfection of cultured cells.

The construction and cloning of a stable full-length dengue cDNA copy in a strain of *Escherichia coli* using the pBR322 plasmid vector was described by Lai, C. J. et al (Lai, C. J.; Zhao, B.; Hori, H. and Bray, M. (1991). "Infectious RNA transcribed from stably cloned full-length cDNA of dengue type 4 virus". Proc. Natl. Acad. Sci. USA. 88: 5139–5143). They verified that RNA molecules produced by in vitro transcription of the full-length cloned DNA template were infectious, and progeny virus recovered from transfected cells was indistinguishable from the parental virus from which the cDNA clone was derived. But, as mentioned in the Patent Application WO 93/06214, such an infectious DNA construct and RNA transcripts generated therefrom were pathogenic, and that the attenuated dengue viruses generated thus far were genetically unstable and had the potential to revert back to a pathogenic form overtime. To solve this problem, the Applicant proposed to construct cDNA sequences encoding the RNA transcripts to direct the production of chimeric dengue viruses incorporating mutations to recombinant DNA fragments generated therefrom. A preferred mutation ablates NS1 protein glycosylation.

The construction of full-length YF 17D cDNA template that can be transcribed in vitro to yield infectious YF virus RNA was described by Rice et al (Rice, C. M.; Grakoui, A.; Galler, R. and Chambers, T. (1989). "Transcription of infectious yellow fever RNA from full-length cDNA templates produced by in vitro ligation". The New Biologist. 1: 285–296). Because of the instability of full-length YF cDNA clones and their toxic effects on *Escherichia coli*, they developed a strategy in which full-length templates for transcription were constructed by in vitro ligation of appropriate restriction fragments. Moreover, they found that the YF virus recovered from cDNA was indistinguishable from the parental virus by several criteria. The YF infectious cDNA is derived from the 17D-204 substrain.

Notwithstanding the YF virus generated from the known YF infectious cDNA is rather attenuated, it cannot be used for human vaccination because of its residual neurovirulence, as determined by Marchevsky, R. S. et al (Marchevsky, R. S.; Mariano, J.; Ferreira, V. S.; Almeida, E.; Cerqueira, M. J.; Carvalho, R.; Pissurno, J. W.; Travassos da Rosa, A. P. A.; Simoes, M. C.; Santos, C. N. D.; Ferreira, I. I.; Muylaert, I. R.; Mann, G. F.; Rice, C. M. and Galler, R. (1995). "Phenotypic analysis of yellow fever virus derived from complementary DNA". Am. J. Trop. Med. Hyg. 52(1): 75–80).

In short, to obtain a YF vaccine virus using recombinant DNA techniques, it is necessary, cumulatively:

(1) to genetically modify the existing YF infectious cDNA;

(2) to assure that the infectious DNA construct and RNA transcripts generated therefrom give rise to virus which is not pathogenic, and, moreover, does not have the potential to revert to a pathogenic form;

(3) the YF virus generated from cloned cDNA, in addition to being attenuated should retain its immunological properties.

Accordingly, an improved YF virus vaccine without neurovirulence and immunogenic generated from a cloned YF infectious cDNA should be developed for human immunization.

SUMMARY OF THE INVENTION

It is an object of the present invention to provide a safe and effective YF virus vaccine obtained from a cloned cDNA having the phenotypic characteristics of the 17DD strain, mainly its attenuation and immunogenicity.

In one embodiment, the present invention relates to a new version of YF infectious cDNA clone that is 17DD-like, which is the most genetically stable substrain of the YF 17D strain.

In another embodiment of the present invention, there is provided new YF plasmids which have the complete sequence of the YF infectious cDNA.

Another embodiment of the present invention is a recombinant YF virus which is regenerated from a YF infectious cDNA.

In another embodiment, the present invention relates to a process for production of a YF vaccine virus by transfecting host cells and recovering 17DD-like virus.

The cDNA template of the present invention resulted of nine mutations which have been introduced in the infectious cDNA named YFiv5.2 (see Rice et al, 1989).

New plasmids, named pYF5'3'IV/G1/2 and pYFM5.2/T3/27, and a method to obtain the same are provided to accomplish the mentioned mutations.

BRIEF DESCRIPTION OF THE DRAWINGS

FIGS. 6A–6H set forth the complete nucleotide sequence of the YF infectious cDNA of the present invention.

FIG. 7 illustrates the methodology for the regeneration of YF virus from cloned cDNA of the present invention.

DETAILED DESCRIPTION OF THE INVENTION

The phenotypic testing of the virus recovered from the 17D-204 substrain cDNA described by Rice et al., 1989 showed that the virus is suitable for mapping virulence determinants as far as reversion to the wild type phenotype is concerned. However, the slightly higher clinical score observed in neurovirulence tests suggests caution in its use for human vaccination (Marchevsky et al, 1995). It is also noteworthy that the YF 204 substrain, used for the preparation of the cDNA library and the infectious cDNA (Rice et al, 1985; 1989), is closely related in terms of lineage and passage number to other YF 204 substrains which brought about most cases of post vaccine encephalitis in vaccinees (Schoub, B. D.; Dommann, C. J.; Johnson, S.; Downie, C. and Patel, P. L. (1990). "Encephalitis in a 13-year old boy following 17D YF vaccine". J. Infection 21: 105–106; Merlo, C., Steffen, R.; Landis, T., Tsai, T. and Karabatsos, N. (1993). "Possible association of encephalitis and a 17D YF vaccination in a 29-year old traveller". Vaccine. 11: 691). In contrast, no cases of post vaccine encephalitis were recorded with the 17DD substrain, even in the early days of vaccination (Fox, J. P.; Lennette, E. H.; Manso, C. and Souza Aguiar, J. R. (1942). "Encephalitis in man following vaccination with yellow fever 17D virus. Am. J. Hyg. 36: 17–142; Fox, J. P. and Penna, H. A. (1943). "Behavior of 17D yellow fever virus in Rhesus monkeys. Relation to substrain, dose and neural or extraneural inoculation". Am. J. Hyg. 38: 52–172).

Figure 2:
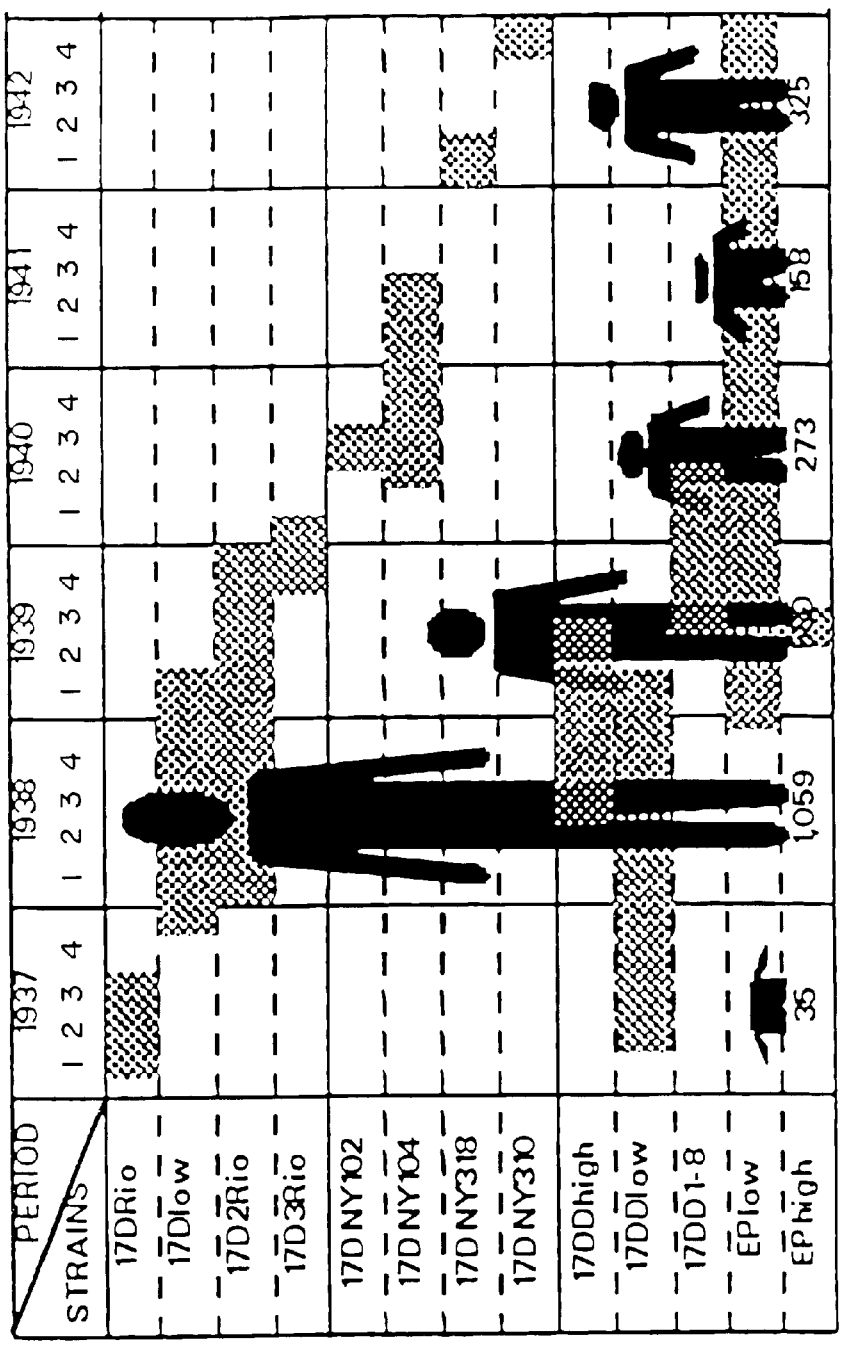
FIG. 2 the use of YF 17DD virus for human immunization during the establishment of the 17D strain in Brazil.

As is evident from Table 1 and FIG. 2 the 17DD substrain was by far the mostly used substrain for both inocula and vaccine production with special emphasis for the EPlow substrain which is still being used nowadays. The complete nucleotide sequence of the genome of 17DD EPlow substrain has been recently derived (Duarte dos Santos et al, 1995) and its comparison with the sequences available for other substrains like 17D-204 (Rice et al, 1985; Despres et al, 1987) and 17D-213 (Duarte dos Santos et al, 1995) provides an estimate of the extent of genetic variability among these strains. The average number of fixed nucleotide or amino acid sequence changes per passage of the virus is significantly lower for DD suggesting that the 17DD strain is genetically more stable than the others (Galler, R. et al, Vaccine, in press) and this may be of importance regarding YF vaccine production.

TABLE 1

Estimated amounts of inocula and vaccine produced with different substrains during the period of 1937–1942 in Brazil

| 17D substrains | Period of use in month | Inocula (ml) | Vaccine (ml) |
|---|---|---|---|
| 17DRio | 8 | 161 | NA |
| 17Dlow | 15 | 132 | NA |
| 17D2Rio | 12 | NA‡ | NA |
| 17D3Rio | 6 | NA | 4,080 |
| 17DDhigh | 11 | 969 | 36,125 |
| 17DDlow | 16 | 365 | 55,778 |
| 17DD1-8 | 12 | Vaccine* | 33,842 |
| 17D-NY102 | 6 | 1,317 | 2,668 |
| 17D-NY104 | 17 | Vaccine | 14,073 |
| 17D-NY318 | 3 | Vaccine | 1,820 |
| 17D-NY310 | 3 | Vaccine | 4,457 |
| 17DD EP | 48 | Vaccine | 11,754 |
| 17DD EPlow⁺ | 48 | NA | 7,097 |
| 17DD EPhigh | 2 | NA | 2,781 |

*Vaccine means that the inocula for the subsequent vaccine production was also a lot of vaccine. The amount of inocula in these cases are not available.
⁺Currently in use for vaccine production at FIOCRUZ
‡NA not available Therefore, in the present invention, mutations have been introduced in the YF infectious clone cDNA, namely YFiv5.2, to make it DD-like. These mutations are located at the following nucleotide position/gene/amino acid:

1140/E/36 (T (Thymine) ⇒Val (Valine)→C (Cytosine) ⇒Ala (Alanine)), 1436, 1437/E/155 (G (Guanine), A (Adenine) ⇒Asp (Aspartic Acid), →A (Adenine), G (Guanine) ⇒Ser (Serine)), 1946/E/335 (T (Thymine) ⇒Ser (Serine)→C (Cytosine) ⇒Pro (Proline)), 2219, 2220/E/409 (A (Adenine), C (Cytosine)⇒Thr (Threonine) →G (Guanine), T (Thymine) ⇒Val (Valine)), 8808/NS5/391 (A (Adenine) ⇒Asn (Asparagine)→G (Guanine) ⇒Ser (Serine)), 9605/NS5/657 (G (Guanine) ⇒Asp (Aspartic Acid)→A (Adenine) ⇒Asn (Asparagine)).

In addition to these mutations, one coding and four silent mutations occured fortuitously at the following nucleotide/gene 2356/E (T (Thymine)→C (Cytosine)), 2602/NS1 (T (Thymine)→C (Cytosine)), 2677/NS1 (C (Cytosine)→T (Thymine)), 2681/NS1 (G (Guanine) ⇒Ala (Alanine)→A (Adenine) ⇒Thr (Threonine)), and 10722 (G (Guanine)→A (Adenine)). Finally, the mutation occuring at nucleotide/gene 8656/NS5 (A (Adenine)→C (Cytosine)) was necessary to create a BstEII site permitting the appropriate ligation and regeneration of the complete genome and, consequently, the recovery of virus.

In the E protein, the creation of a N-linked glycosylation site at amino acid E/155 (nt), which is located in domain I (as defined in Rey, F. A. et al), might influence the fusogenic activity of the E protein as observed for a dengue type 2 virus that had that site eliminated by mutation. This is so because E proteins, in absence of sugar moiety, have a higher pH threshold and would therefore fuse to the endosomal membrane more easily and thereby allow the viral cycle to proceed. In this regard, the YF virus 17D-204 vaccine consists of a mixed population of viruses with or without that glycosylation site in contrast to the 17DD and 17D-213 viruses (see Post, P. R.; Santos, C. N. D.; Carvalho, R.; Cruz, A. C. R.; Rice, C. M. and Galler, R. (1992). "Heterogeneity in envelope protein sequence and N-linked glycosylation among Yellow Fever virus vaccine strains. Virology. 188: 160–167). For the construction of the infectious YF cDNA a population devoid of this site was selected. It is noteworthy that a 17D-204 virus that caused a fatal human case of post vaccinal encephalitis also had no N-linked glycosylation site due to mutation (see Jennings, A. D.; Gibson, C. A.; Miller, B. R.; Mathews, J. H.; Mitchell, C. J.; Roehrig, J. T.; Wood, D. J.; Taffs, F.; Sil, B. K.; Whitby, S. N.; Monath, T. P.; Minor, P. D.; Sanders, P. G. and Barrett, A. D. T. (1994). "Analysis of a yellow fever virus isolated from a fatal case of vaccine-associated human encephalitis". J. Infect. Dis. 169: 512–518).

Figure 3:
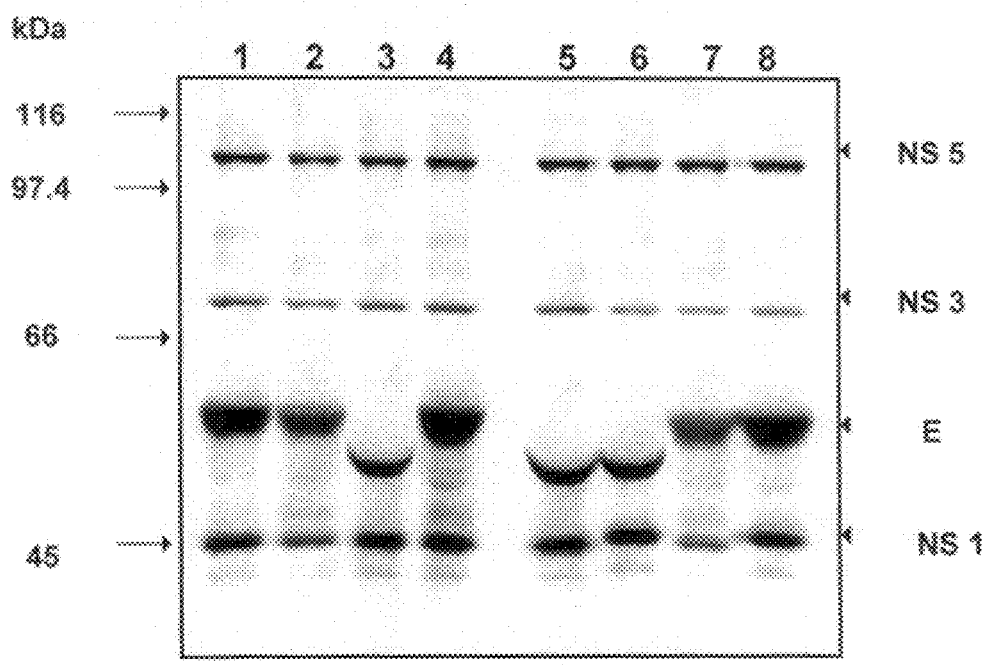
FIG. 3 shows the analysis of viral E protein N-linked glycosylation on denaturing polyacrylamide gel.

FIG. 3 shows a gel of immunoprecipitation of [$^{35}$S] methionine labeled viral proteins of two Yellow Fever vaccine strains and of Yellow Fever Virus infectious clones. VERO cells were infected at an MOI of 1. At 48 hours post-infection, cell monolayers were pulsed-labeled with [$^{35}$S] methionine for 1 hour. Detergent cell extracts were immunoprecipitated with yellow fever-specific mouse hyperimmune antiserum (obtained from ATCC). All immunoprecipitates were collected using protein A-sepharose. Samples were analysed by 10% sodium dodecyl sulfate polyacrylamide gel electrophoresis and by fluorography and exposition at −70° C. The numbers on the lanes correspond to: (1) vaccine strain 17DD; (2) infectious clone A5/2-T3; (3) infectious clone A5/T3; (4) vaccine strain 17D-213; (5) infectious clone G1/5.2; (6) infectious clone A5-T3/27; (7) infectious clone G1/2-T3 N/S; (8) infectious clone G1/2-T3/27. The positions of molecular weight markers are shown on the left and the yellow fever viral proteins on the right.

The potential role of the other changes in the E protein sequence for the complete attenuation of the virus recovered from cDNA is less clear.

Regarding the 2 alterations in the NS5 protein, there are no structural analyses available to date and it is, therefore, difficult to predict the effect of any particular amino acid change in its conformation/function. However, the mutation at amino acid 657 from the NS5 amino terminus is only 8 amino acids away from the putative catalytic site of the RNA replicase, the Gly-Asp-Asp (Glycine-Aspartic Acid-Aspartic Acid) motif, which is conserved throughout viral RNA polymerases from plant to animal viruses. It would not be surprising if this mutation has somewhat altered the activity of the enzyme leading to better RNA replication kinetics in the infected cell and consequently a higher viral output.

Figure 1:
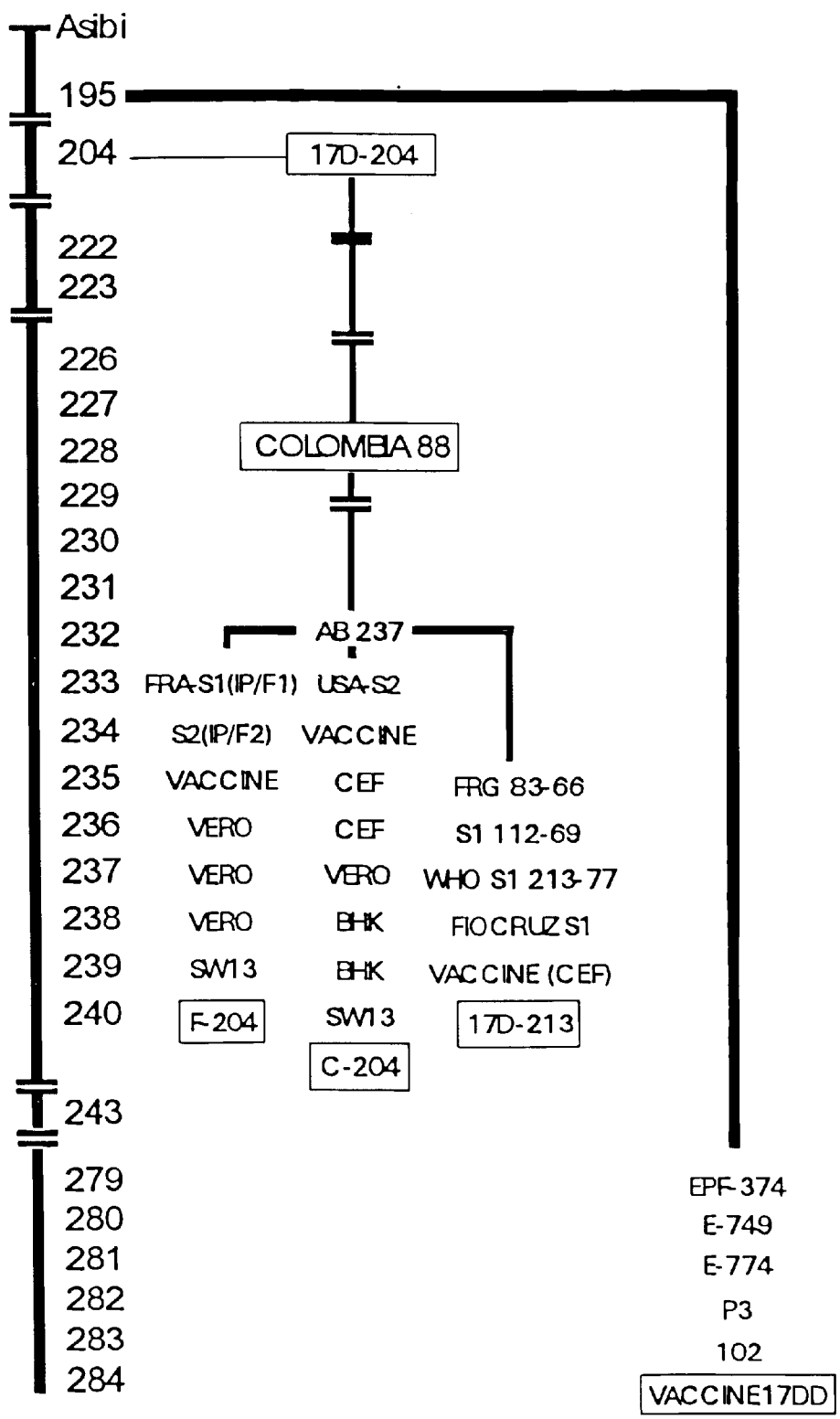
FIG. 1 illustrates the passage history of the original YF Asibi strain and derivation of YF 17D vaccine strains.

The mutations at nt sites 1140, 1436, 1437, 1946, 2219, 2220, 8808 and 9605 have been introduced in the YF infectious cDNA YFiv5.2. The YF infectious cDNA in its known version exists in the form of two plasmids bearing the extreme 5' and 3' end sequences (pYF5'3'IV) and the genome middle region (pYFM5.2) as described by Rice, C. M. et al (Rice et al, 1989). The construction of these YF plasmids required the ligation of several cDNA fragments present in different plasmids of the cDNA library. The virus that gave rise to this cDNA library had been twice plaque purified in CEF cultures and the titer amplified by consecutive passages in Vero, BHK and SW13 cells, once each (see FIG. 1). The extent of genetic variability in the viral population used for RNA extraction is not known. However, the complete nucleotide sequence analysis of the final infectious cDNA plasmids provided the identification of nucleotide changes not present in any other 17D virus for which genomic sequences are available. Due to stability problems, it was impossible to include the whole YF genome in one single plasmid and therefore a two-plasmid system and in vitro ligation of purified restriction fragments to regenerate the complete genome was established (see Rice, C. M. et al, 1989).

Plasmid pYF5'3'IV contains the YF 5' terminal sequence (nt 1–2271) adjacent to the SP6 phage polymerase promoter and 3' terminal sequence (nt 8276–10862) adjacent to the XhoI site used for production of run off transcripts (see FIG. 2 in Rice, C. M. et al, 1989). The plasmid pYFM5.2 contains YF 17D cDNA from nt 1372 to 8704.

Figure 4:
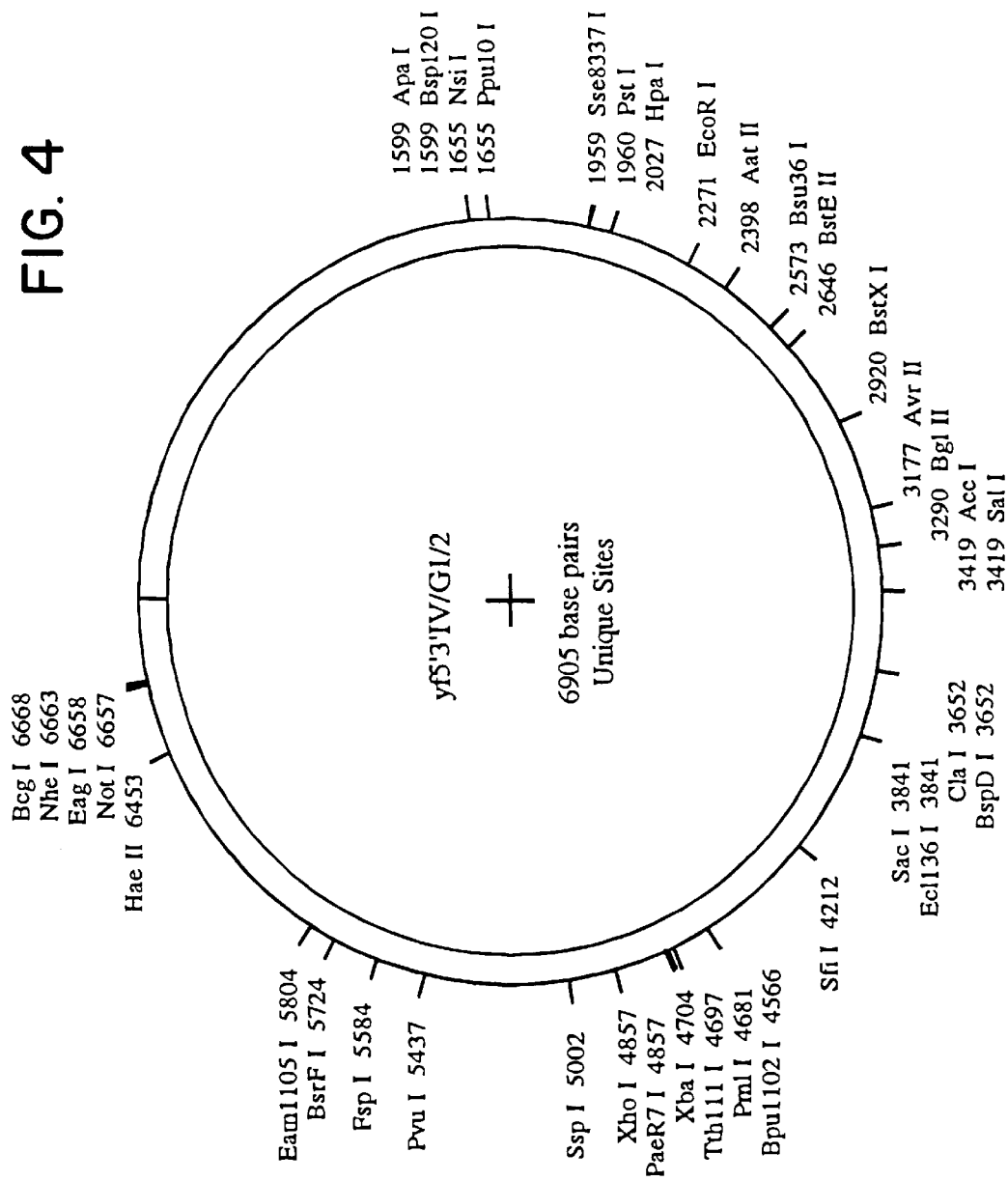
FIG. 4 shows the structure of plasmid pYF5'3'IV/G1/2 bearing the extreme 5' and 3' end sequences of the infectious cDNA of the present invention.

The pYF5'3'IV/G1/2 plasmid is prepared from pYF5'3'IV by creating changes, in the YF 5' terminal sequence, at nucleotides 1140 and 1436/1437, and in the 3' terminal sequence, at nucleotides 8656 and 9605 (see Table 2). The remaining of the plasmid consists of pBR 322 with a deletion from the AatII to the EcoO109 sites which resulted in the destruction of both sites. This plasmid contains a unique AatII site corresponding to nt 8406 of the YF 17D cDNA. To accomplish the changes, two separate rounds of cloning/mutagenesis steps were necessary to create the relevant mutations in the E and NS5 proteins. The E mutations were introduced by cloning a XbaI/PstI fragment into pAlter™ (Promega, Inc.) and restriction fragment exchanging with ApaI/NotI. The NS5 changes were introduced by cloning/mutagenesis of an EcoRI/SstI fragment in pAlter and swapping it back into the original plasmid using the same enzymes. The structure of plasmid pYF5'3'IV/G1/2 is shown in FIG. 4.

TABLE 2

YF plasmid genetic modification.

| Plasmid | Nucleotide changes[a] | |
|---|---|---|
| YF5'3'IV | G1/2 | 1140 |
| | | 1436/1437 |
| | | 8656, 9605 |
| YFM5.2 | T3/27 | 1946 |
| (Plasmid extended 719 | | 2219/2220 |
| nucleotides to the unique | | 8656 |
| SalI site- T3 series) | | 8808 |

[a]All changes were confirmed by nucleotide sequence determination on plasmid DNA and cDNA from recovered virus.

Figure 5:
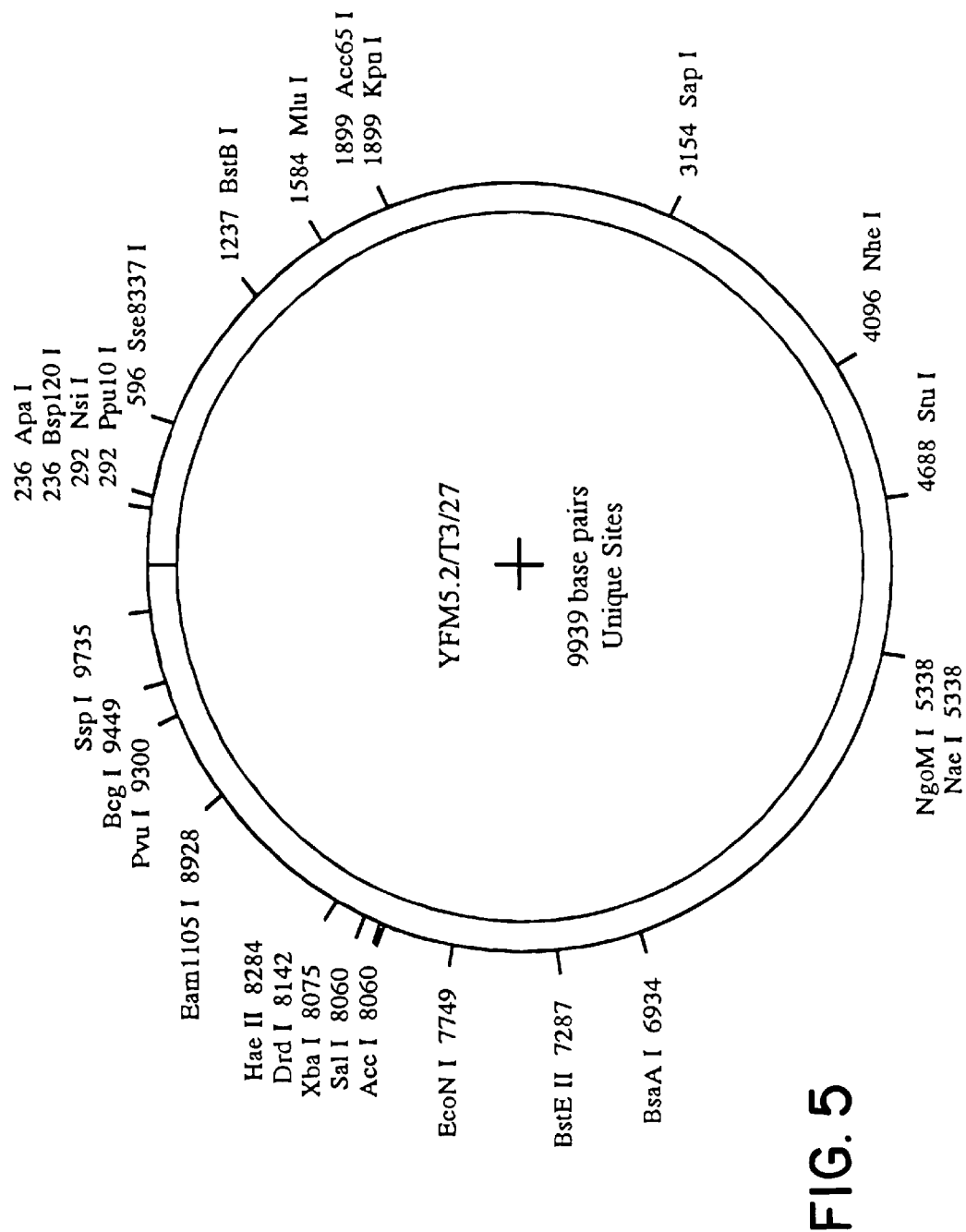
FIG. 5 shows the structure of plasmid pYFM5.2/T3/27 bearing the genome middle region of the YF infectious cDNA of the present invention.

The plasmid pYFM5.2/T3/27 is prepared from pYFM5.2 by introducing the changes at nucleotides 1946, 2219/2220, 8656 and 8808. To accomplish the nucleotide changes, it was introduced into pYFM5.2 an AatII/SalI fragment encopassing YF nts 8406–9423 rendering this plasmid 719 nucleotide longer than its parental plasmid pYFM5.2. Since the SalI is also present at the same nucleotide position in the YF sequences contained in the other YF plasmid (pYF5'3'IV) it became possible to use a combination of ApaI or NsiI and SalI to produce the relevant restriction enzyme fragments. The intermediate plasmid pYFM5.2/T3 was used to derive the T3/27 plasmid which contains the changes at nucleotides 1946 (T→C), 2219 (A→G) and 2220 (C→T) as compared to the parental YFiv 5.2 (see Table 3). The structure of plasmid pYFM5.2/T3/27 is shown in FIG. 5.

brate cells. The black area corresponding to the vector sequences contain the beta-lactamase gene and the origin of replication. The position of the SP6 promoter is shown and is adjacent to the first 5' nucleotide of the YF genome. Nucleotides 1–1603 (down to the ApaI site) and 9424 (SalI) to 10862 (XhoI) come from plasmid G1/2 whereas nucleotides from 1604 (ApaI) to 9423 (SalI) come from plasmid T3/27.

Besides pBR 322, other vectors which provide the stabilization of the YF virus genome can be used to prepare the plasmids of the present invention. Specific examples include

TABLE 3

Comparison of YF infectious plasmid clone sequences.

| NT/gene | YFiv5.2[a] | DD[b] | YFiv5.2/DD[c] | NT ⇒ | | AA | |
|---|---|---|---|---|---|---|---|
| 1140/E | T | C | C | T ⇒ | Val → | C ⇒ | Ala |
| 1436,1437/E | G,A | A,G | A,G | G,A ⇒ | Asp → | A,G ⇒ | Ser |
| 1946/E | T | C | C | T ⇒ | S → | C ⇒ | P |
| 2219,2220/E | A,C | G,T | G,T | A,C ⇒ | Thr → | G,T ⇒ | Val |
| 2356/E | T | T | C | | | — | |
| 2602/NS1 | T | T | C | | | — | |
| 2677/NS1 | C | C | T | | | — | |
| 2681/NS1 | G | G | A | G ⇒ | Ala → | A ⇒ | Thr |
| 8656/NS5 | A | A | C | | | — | |
| 8808/NS5 | A | G | G | A ⇒ | Asn → | G ⇒ | Ser |
| 9605/NS5 | G | A | A | A ⇒ | Asp → | G ⇒ | Asn |
| 10454 | G | A | A | | | — | |
| 10722 | G | G | A | | | — | |

[a]Rice at al (1989)
[b]Duarte dos Santos et al (1995)
[c]Ferreira, II and Galler, R. (unpublished).

Figure 8:
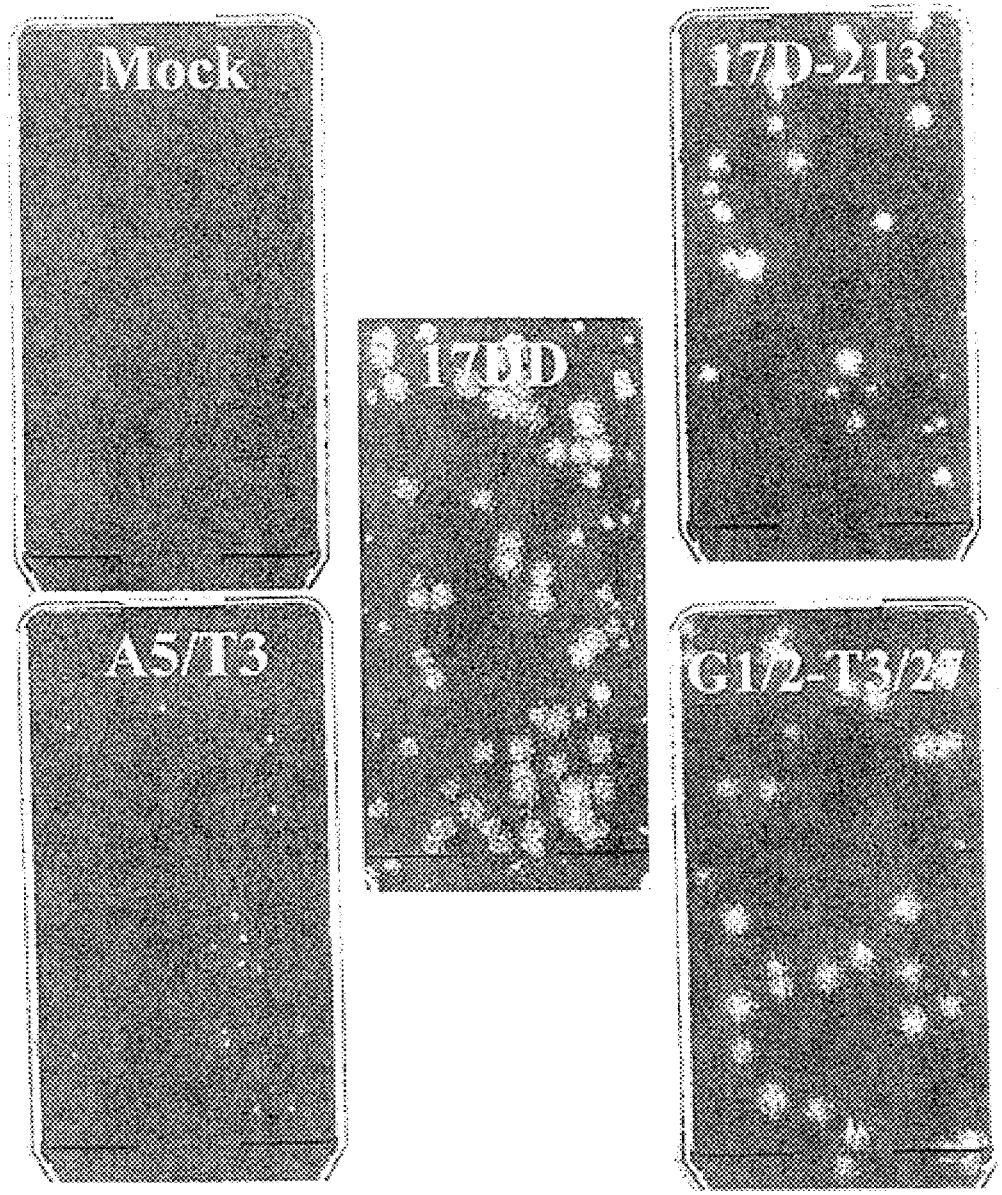
FIG. 8 displays the comparative plaque size analysis among YF 17D viruses.

The BstEII site at YF nt 8656 was created in both YF plasmids and their digestion with ApaI or NsiI and BstEII provides the appropriate restriction enzyme fragments for the Ligation and regeneration of the completer genome of virus. This features constitutes another genetic marker for this new version of the YF infectious cDNA. The complete nucleotide sequence (SEQ ID NO:1) of YF infectious cDNA (YFiv5.2/DD) is shown in FIG. 8. Deposit of plasmids pYF5'3'IV/G1/2 and pYFM5.2/T3/27 has been made at the American Type Culture Collection and they are identified by ATCC Accession No. 97771 and 97772, respectively.

Figure 7:
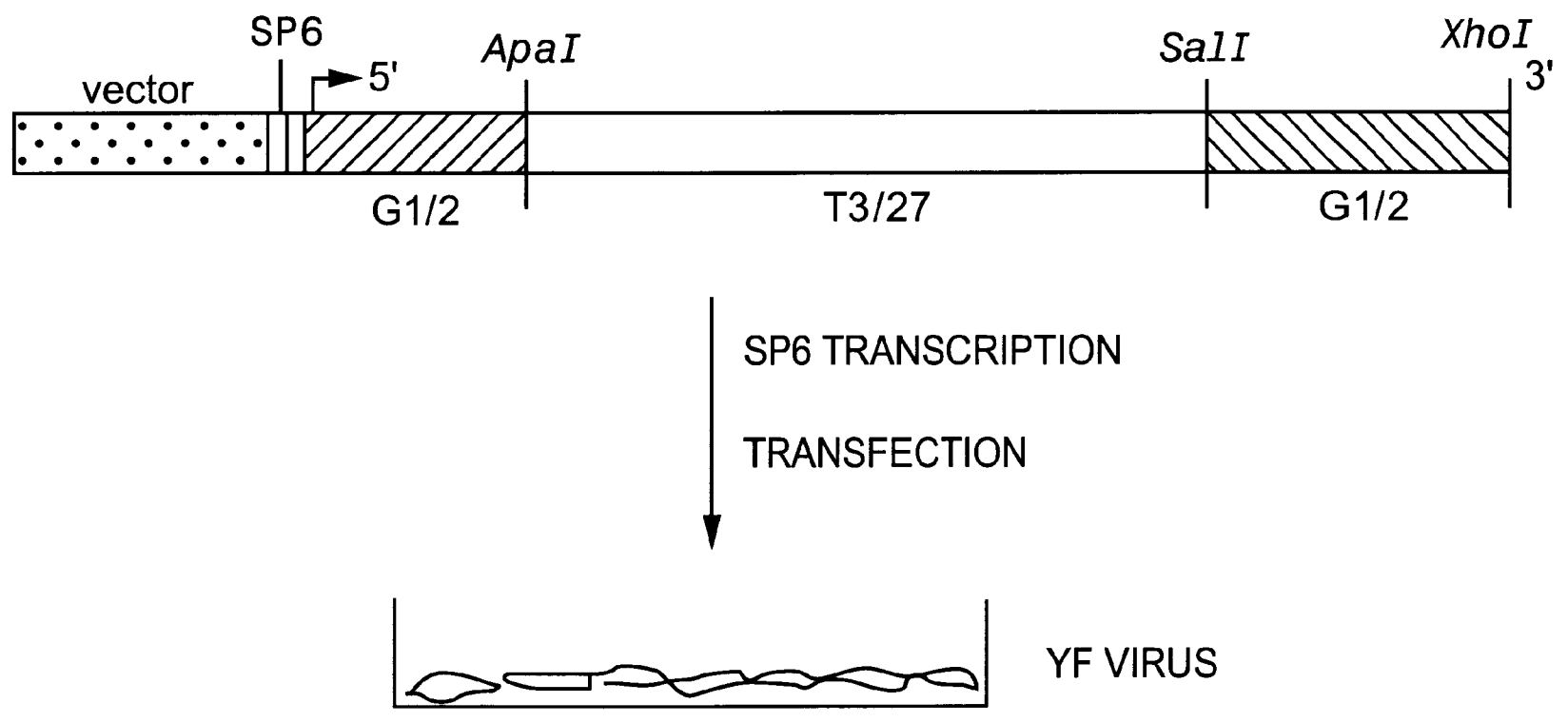

FIG. 7 shows the methodology for the regeneration of YF virus from cloned complementary DNA. The plasmids G1/2 and T3/27 shown in FIGS. 4 and 5 are digested with ApaI and SalI to produce restriction fragments which are purified, ligated and digested with XhoI. The resulting DNA corresponds to full-length YF cDNA template that can be used for in vitro transcription with SP6 polymerase to produce infectious RNA transcripts upon transfection of cultured verteplasmids such as pBR 325, pBR 327, pBR 328, pUC 7, pUC 8, pUC 9, pUC 19, phages such as λ phage, M13 phage and the like.

Templates were prepared from pYF5'3'IV/G1/2 and pYFM5.2/T3/27 using ApaI/SalI and NsiI/SalI to produce the restriction fragments for in vitro ligation. After digestion with XhoI to linearize the ligated DNA, the template was used for in vitro transcription. Virus has been recovered after RNA transfection of cultured animal cells.

The virus regenerated from plasmids pYF5'3'IV/G1/2 and pYFM5.2/T3/27 will be hereinafter referred to as YFiv5.2/DD.

Similarly to YF 17DD and 17D-213 the new virus produces large plaques in Vero cells in contrast to the 17D virus recovered from the original cDNA (Yfiv5.2; see FIG. 8) In ten consecutive passages of this virus in CEF cells this large plaque phenotype was shown to be stable. In addition, there was no alteration in its neurovirulence for mice as compared to the other well

TABLE 4

Mouse[a] neurovirulence and neuroinvasiveness of YF 17D viruses

| | route of inoculation | | | | | |
|---|---|---|---|---|---|---|
| | intracerebral | | | intranasal | | |
| virus | inoculum (PFU/ml[b])[c] | deaths | average survival time | inoculum (PFU/ml)[c] | deaths | average survival time |
| 17DD[d] | 6.5 × 10⁵ | 7/8 | 10.43 ± 1.13 | 6.5 × 10⁶ | 1/10 | N.A[h] |
| 17D-213[e] | 2 × 10⁶ | 8/8 | 8.50 ± 1.07 | 2.1 × 10⁷ | 2/10 | 16.5 days |

TABLE 4-continued

Mouse[a] neurovirulence and neuroinvasiveness of YF 17D viruses

| | route of inoculation | | | | | |
|---|---|---|---|---|---|---|
| | intracerebral | | | intranasal | | |
| virus | inoculum (PFU/ml[b])[c] | deaths | average survival time | inoculum (PFU/ml)[c] | deaths | average survival time |
| 17D-204/A5-T3[f] | $4.75 \times 10^5$ | 8/8 | $8.50 \pm 0.93$ | $4.75 \times 10^6$ | 0/9 | N.A[h] |
| 17D-204/G1/2-T3/27[g] | $1.3 \times 10^6$ | 8/8 | $8.50 \pm 0.93$ | $1.3 \times 10^7$ | 0/14 | N.A[h] |

[a]Swiss inbred mice, 3-week old (11 g).
[b]pfu = plaque-forming unit
[c]inoculum of 20 μl each i.c and i.n.
[d]Current substrain used for YF vaccine production the sequence of which base the genetic modifications introduced into the first YF infectious cDNA.
[e]An early experimental tissue culture vaccine strain, it is also the WHO substrain.
[f]This substrain corresponds to the original virus derived from the first version of the YF infectious cDNA.
[g]Current version of the virus progeny from the genetically modified infectious cDNA clone.
[h]N.A = not available The animal cell culture used herein may be any cell insofar as YF virus 17D strain can replicate. Specific examples include, Hela (derived from carcinoma of human uterine cervix), CV-1 (derived from monkey kidney), BSC-1 (derived from monkey kidney),RK 13 (derived from rabbit kidney), L929 (derived from mouse connective tissue), CE (chicken embryo) cell, CEF (chicken embryo fibroblast), SW-13 (derived from human adrenocortical carcinoma), BHK-21 (baby hammster kidney), Vero (african green monkey kidney), LLC-MK2 (derived from Rhesus monkey kidney (Macaca mulata)), etc.

Therefore, according to one of the embodiments of the present invention, a protocol was stablished leading from nucleic acid to YF vaccine virus production under Good Manufacturing Practices (GMP) by transfecting cells certified for human vaccine production and recovering 17DD-like virus. This virus was then used to produce primary and secondary seed lots in primary cultures of chicken embryo fibroblasts under GMP. The virus resulting from seed lots is tested for monkey neurovirulence. This work should set the precedent for the production of new live attenuated flaviviruses from cloned cDNA considering that infectious clones are now available for several of them with special emphasis on dengue and japanese encephalitis.

The work carried out to produce the original, primary and secondary seed lots is detailed in Example 5.

The production of YF vaccine based on the seed lot system has arisen from the necessity of having reliable virus regarding human vaccination. Thus, the concept of the seed lot system was the first break-through in the development of the YF vaccine. In the period of 1937–1942, the scientists which were working with the establishment of YF vaccine production did use a number of viral 17D substrains (17D Rio, 17Dlow, 17D2Rio, 17D3Rio, 17DD, 17DDhigh, 17DDlow, EP, EPlow, EPhigh, NY102, NY104, NY 310/318). As production and the vaccination campaigns went on and complications with vaccinees were noted it was realized the possibility of phenotypic selection of viruses by serial passage in tissue culture. When checking early records of vaccine production at FIOCRUZ, we have noticed that for all substrains more inocula was prepared than what was actually used for vaccine production and therefore vials of specific passages were usually available (Post, P R. and Galler, R., unpublished). This operating procedure together with the use of multiple strains at one time in a way did allow them to have uninterrupted production. With the observation of post-vaccinal complications in humans and also the failure of some viruses in the quality control tests (neurovirulence for monkeys) as described by Fox et al (1942) and Fox and Penna (1943) it became imperative to reduce the variables during vaccine production. One of the possibilities was to reduce the viral passages used for production. That was accomplished by establishing the seed lot system in which the virus is kept at defined passage levels whereas that particular passage is quality tested. In the records we have noted that the primordial fact that led to this development was the observation that high passages of DD substrain (named DDhigh) led to the loss of immunogenicity in human vaccinees with deficient coverage of the local population against wild type YF (Fox & Penna, 1943). This observation led the scientists back to the initial passages of DD substrain, more precisely at sc 229/230, which was then used to prepare 8 consecutive inocula (named DD1 to 8). Each of these DD substrains were cultivated for not more than 30 passages. Every passage was actually used for vaccine production but to different extents. The procedure yielded reliable virus regarding human vaccination. At this stage the NY104 substrain was the one being used for most production of vaccine and therefore this change in operation was implemented and NY104 was the first substrain to be fully employed in the seed lot system. It is illustrative to such operating practice that only 3 seed lots (E688, E694 and E716) were used to produce almost 2 million doses of vaccine during a 10-month time interval. Unfortunately, some of these vaccine batches turned out to be extremely neurotropic (Fox et al, 1942; Fox & Penna, 1943) and the use of this substrain was discontinued.The next strain in line was EPlow which was used at sc243 to produce inocula in embryonated eggs instead of chicken embryonic tissue without nervous sytem. There were 150 serial passages of EPlow in embryonated eggs but only 7 of these passages were used for vaccine production. Virus produced in that way performed well in monkey neurovirulence tests and in human trials. Therefore, EPlow at chicken embryo passage 35 was used to prepare the EPF374 vaccine which later gave rise to the DD primary and secondary seed lots under use nowadays, which are just 2 passages ahead of the original seed over a time period of 50 years.

In a preferred embodiment of the present invention, to accomplish the YF 17D vaccine virus propagation in cells certified for the production of human vaccines, primary cultures of chicken embryo fibroblasts (CEF) were used in all production steps. There are several reasons to use CEF cells: these cells have been used successfully for measles vaccine production for years with extensive experience in its preparation and quality controls; a number of Standard Operating Practices (SOPs) is available. Moreover, the production of YF vaccine in CEF cultures led to 3 consecutive lots of vaccine that passed all tests including neurovirulence for monkeys.

The stabilization of the YF 17D genome as DNA not only will reduce the accumulation of mutations in the viral genome as seed lots are produced to replace the previous one but will also provide a much more homogeneous population in terms of nucleotide sequence and consequently in terms of phenotypic markers including attenuation for humans.

As mentioned before, in a preferred embodiment, all lots were prepared in primary cultures of chicken embryo fibroblasts (CEF) using eggs derived from SPF (Specific Pathogen Free) flocks. Cell cultures were set up in a suitable medium and used later post-seeding. Viruses were recovered after incubation by centrifugating and removing the cellular debris. To the supernatant containing the viruses was added a stabilizer which is, for the skilled in the art, known to enhance the stability of viral immunogenic compositions. All viruses are stored at −70° C.

The following examples are illustrative of the invention and represent preferred embodiments. Those skilled in the art may know, or be able to find using no more than routine experimentation, to employ other appropriate materials and techniques, such as the above mentioned vectors, cultured cells and transfection methods.

EXAMPLE 1

Preparation of Plasmids DNAs a) Derivation of Plasmid pYF5'3'IV

As described in Rice et al, 1989, plasmid pYF5'3' IV contains the 5' terminal YF sequence (nt 1–2271) adjacent to the SP6 promoter, and the 3' terminal sequence (nt 8276–10862) adjacent to the XhoI site, which is used to linearize the template and thereby allow the production of run-off transcripts, all introduced in the pBR322 sequence. The original plasmids from which the 5' terminal YF sequence was derived are: pYF5' ext#20 (nt 1–536), p$28_{III}$ (nt 537–1964), and p$10_{III}$ (nt 1965–2271). p$35_{III}$ (nt 8276–8732), p$34_{III}$ (nt 9658–10223), pYF3'ext.#17 (nt 10224–10708) and pYF3'1 #12 (nt 10709–10862) were the original plasmids to derive the 3' terminal YF sequence (Rice et al, 1989). Plasmid pYF5'3'IV contains a unique AatII site corresponding to nt 8406 of the YF 17D cDNA.

b) Derivation of Plasmid pYF5'3'IV/G1/2 pYF5'3'IV/G1/2 was prepared from pYF5'3'IV by carrying out two separate rounds of cloning/mutagenesis to create the changes in nucleotides 1140, 1436/1437 in E protein, and in nucleotides 8656, 8808 and 9605 in NS5 protein. The former genetic changes were carried out by cloning a XbaI/PstI fragment into pAlter (Promega Corp.) and replacing the original sequence with the mutant one by restriction fragment exchange using ApaI/NotI. The NS5 changes were introduced by cloning/mutagenesis of an EcoRI/SstI fragment in pAlter and swapping it back into the original plasmid using the same enzymes.

c) Preparation of Plasmid pYFM5.2

The pYFM5.2 plasmid used was also described in Rice et al, 1989. The original plasmids from which the nucleotide sequence 1372–8704 of YF 17D cDNA was derived are: p$9_{II}$ (nt 1372–1603), p$10_{III}$ (nt 1604–3823), p$3_{III}$ (nt 3824–6901), p$9_{II}$ (nt 6902–7888) and p$35_{III}$ Xho⁻#19 (nt 7889–8704).

p$35_{III}$ Xho_#19 was constructed from p$35_{III}$ in which a silent C to T change at nt 8212 was introduced to destroy the XhoI site in the YF cDNA as to allow the use of XhoI to linearize the DNA templates and consequently the production of run-off transcripts.

d) Derivation of Plasmid pYFM5.2/T3/27 pYFM5.2/T3/27 was prepared from pYFM5.2 by introducing an AatII/SalI fragment which encopasses YF nts 8406–9423 and creating a BstEII site at YF nt 8656. A second mutation was introduced at position 8808 in NS5 protein.

Since digestion of plasmid DNAs with AatII is dificult because it is a very finicky and expensive enzyme, a BstEII site was created at YF nt 8656 in both YF plasmids, following a digestion with ApaI or NsiI to produce the appropriate restriction enzyme fragments for the ligation and regeneration of the complete genome, allowing the recovery of virus. This can also be accomplished when the restriction fragments are produced by digestion with ApaI or NsiI and SalI.

The structure of each plasmid is shown in FIGS. 3 and 4 and the complete sequence of the YF coding sequences for each plasmid is given in FIG. 5.

A comparison between the original YF infectious plasmid clone, YF 17DD strain and the YF infectious cDNA clone, YFiv5.2/DD, sequences is shown in Table 3.

e) Preparation of Large Amounts of Plasmid DNA

To prepare plasmids DNAs from bacteria, glycerol stocks of the *E. coli* harboring each of the two YF plasmids must be available. Luria Broth-50% glycerol media is used in the preparation of the stocks, which are stored at −70° C. Frozen aliquots of the pDNA are also available.

The bacteria are grown in 5 ml LB containing ampicillin (15 μg/ml) overnight at 37° C. This is used to inoculate 1:100 large volumes of LB (usually 100–200 ml). At $OD_{600}$ of 0.8, chloramphenicol is added to 250 μg/ml for the amplification of the plasmid DNA overnight. The plasmid is extracted using the alkaline lysis method. The final DNA precipitate is ressuspended in TE (Tris-EDTA buffer) and cesium chloride is added until a refraction index of 1.3890 is reached. The plasmid DNA is banded by ultracentrifugation for 24 hours. The banded DNA is recovered by puncturing the tube, extracting with butanol and extensive dialysis.

The yields are usually 1 mg of pDNA/liter of culture for pYF5'3'IVG1/2 and 0.2 mg/liter for pYFM5.2/T3/27.

EXAMPLE 2

Preparation of DNA Template

The template to be used for the regeneration of YF 17D virus is prepared by digesting the plasmid DNA with NsiI and SalI (Promega Inc.) in the same buffer conditions, as recomended by the manufacturer. Ten μg of each plasmid are digested with both enzymes (the amount required is calculated in terms of the number of pmol-hits present in each pDNA in order to achieve complete digestion in 2 hours). The digestion is checked by removing an aliquot (200 ng) and running it on 0.8% agarose/TAE gels. When the digestion is complete, the restriction enzymes are inactivated by heating.

The DNA fragments are ligated at a concentration of 20 μg/ml for each fragment and T4 DNA ligase to 5 U/ml. Ligation is allowed to proceed overnight at 15° C. The ligation mixture is heated to 65° C. for 20 minutes to inactivate the T4DNA ligase and an aliquot taken out (200 ng).

Further digestion of the DNA resulting of the ligation is carried out by the use of XhoI, and is performed with buffer conditions adjusted according to the manufacturer (Promega) specifications in order to linearize the template. The resulting product is thereafter phenol-chloroform extracted and ethanol precipitated.

The precipitate is washed with 80% ethanol and resuspended in sterile RNase-free Tris-EDTA buffer.

A template aliquot is taken for agarose gel analysis together with commercial markers for band sizing and quantitation. The template is stored at −20° C. until use for in vitro transcription.

EXAMPLE 3

RNA Transcription from cDNA Template of the Present Invention

RNA transcripts were prepared by using DNA template of the present invention, in a similar manner as described in Konarska et al, 1984 and in Rice et al, 1987 (Konarska, M. M.; Padgett, R. A.; Sharp, P. A. (1984) "Recognition of cap structure in splicing in vitro of mRNA precursors". Cell. 38: 731–736; Rice, C. M.; Levis R.; Strauss, J. H.; Huang, H. V. (1987) "Production of infectious RNA transcripts from Sindbis virus cDNA clones: Mapping of lethal mutations, rescue of a temperature-sensitive marker, and in vitro mutagenesis to generate defined mutants. J Virol 61: 3809–3819). The reaction was allowed to proceed at 39° C. for 1 hour. The mix is extracted with phenol-chloroform twice and the nucleic acid recovered by precipitation with ethanol. The precipitate is resuspended in sterile RNase-free water and an aliquot taken for specific infectivity determination.

EXAMPLE 4

RNA Transfection

Transfection of CEF is carried out using LipofectAMINE® (Life Technologies catalogue # 18324–012. It is a 3:1 (w/w) liposome formulation of the polycationic lipid 2,3-dioleyloxy-N-[2(sperminecarboxiamido)ethyl]-N-N, dimethyl-2,3-bis(9-octadecenyloxy)-1-propanaminium trifluoro acetate) and the neutral dioleoylphosphatidyl ethanolamine (DOPE) in membrane-filtered water) at a concentration of 20 $\mu$g/ml in RNase-free PBS. PBS—phosphate buffer saline—is prepared and sterilized by autoclaving at 121° C. for 20 minutes. The LipofectAMINE is pipeted into a polystyrene 5 ml tube containing PBS. Primary CEF cells are seeded and used 24 hours post seeding.

The transcription mix is added to the cell culture monolayer dropwise. Cells are incubated for 20 minutes at room temperature. Thereafter, the mix is removed by aspiration, washed with PBS and incubated for 72 hours in 199 medium.

The culture supernatant constitute the viral stock after addition of stabilizer. The viral stock is tested for sterility, toxicity, potency and for the presence of adventitious agents. The viral stock is the original seed lot.

The specific infectivity of the transcripts is deduced from experiments in which serial dilutions of the RNA are transfected into Vero cells and these are overlaid with semi-solid medium. Staining with crystal violet for the counting of plaques and knowing the amount of RNA, as determined by measuring the OD (otic density) at 260 nm, will alow the determination of specific infectivity of the transcripts (PFU/ $\mu$g total RNA).

This determination is relevant to establishing the multiplicity of infection events that lead to the original stock. It ensures an acceptable number of events equivalent to infection with live virus in order to reduce the probability of accumulation of mutations in the viral genome given the high number of replication cycles due to low RNA input.

There are currently two methods for an efficient transfection of cultured cells with RNA. One is lipid-mediated and the other is electroporation. In the lipid-mediated method, LipofectAMINE or Lipofectin are normally used. A series of experiments using viral RNA extracted from YFiv5.2/DD-infected Vero cells allowed the comparison of the efficiency of Lipofectin and LipofectAMINE as well as the amount of RNA which provide the highest transfection yields (measured by specific infectivity titers) as related to the concentration of lipid used (concentrations ranging from 10 to 40 $\mu$g/ml). LipofectAMINE is the reagent used in the present invention because it had the highest performance. The amount of RNA to be used cannot be very high. There is a limit in the amount of RNA that can be mixed with a corresponding amount of lipid to reach the best transfection efficiency, and, in consequence, the highest specific infectivity. In the present invention, it is used a ratio of the reagents ranging 0.5–2 $\mu$g of total RNA: 10–40 $\mu$g of LipofectAMINE per 1 ml of PBS.

EXAMPLE 5

Preparation of Seed Lots

All lots were prepared in primary cultures of CEF using eggs derived from SPF (Specific Pathogen Free) flocks. Viruses were recovered by pooling the medium present in each T-flask into centrifuge bottles and spinning at low speed to remove cellular debris. The supernatant was aspirated into 1 L flasks containing estabilizer at 1:1 ratio and frozen slowly by rotating on an ethanol dry ice bath after removal of all quality control aliquots. All viruses are stored at −70° C.

Preparation of the Original Seed Lot

The original seed lots consists of 3 separate transcription/transfection experiments carried out on different days with different bacthes of primary CEF cultures.

Primary chicken embryo fibroblasts were seeded. A total of 3 disposable T-flasks of 175 $cm^2$, containing in vitro transcribed RNA were transfected into CEF cells using LipofectAmine™. Each T-flask provided a total of 80 ml of culture supernatant. In three separate transfections performed at different days and therefore with different lots of CEF cells titers for the original seed lots were: T1, $10^{4.66}$ (4.66 $log_{10}$ pfu/ml); T2, $10^{4.87}$ (4,87 $log_{10}$ pfu/ml); T3, $10^{5.46}$ (5.46 $log_{10}$ pfu/ml). Each lot provided a total volume of 480 ml of original virus. Eighty ml were used for quality control remaining 400 ml for the preparation of primary seed lot(s).

Preparation of Primary Seed Lot

Two primary seed lots were prepared and named LP1 and LP2. LP1 derives from original seed lot T3 whereas LP2 derives from T2. Each was tested for sterility, potency and adventious agents with satisfactory results. The obtained volumes and titers are:

| Seed lot | Volume (ml) | Titer (log$_{10}$ pfu/ml) |
|---|---|---|
| LP1 | 1.200 | 6.22 |
| LP2 | 1.600 | 6.20 | pfu = plaque-forming unit

Secondary Seed Lots

Three secondary seed lots were prepared and named LS1, LS2 and LS3. LS1 and LS2 derive from primary seed lot LP1 whereas LS3 derives from LP2. Each was tested for sterility, potency and adventious agents with satisfactory results. The obtained volumes and titers are:

| Seed lot | Volume (ml) | Titer (log$_{10}$ pfu/ml) |
|---|---|---|
| LS1 | 5.200 | 6.20 |
| LS2 | 5.600 | 6.05 |
| LS3 | 5.200 | 6.73 |

Each of these seed lots should suffice for YF vaccine production using current manufacturing methodology (embryonate eggs) or the cellular system (CEF cells) for nearly 50 years at a rate of at least 50 million dosis/year.

The foregoing provides a description of the preferred embodiments, however, it should be noted that numerous structural changes and modifications may be made without departing from the spirit and scope of the present invention.

---

What is claimed is:

1. A vaccine composition for humans against yellow fever infection comprising a recombinant YF virus which is regenerated from YF infectious cDNA having the base sequence set forth in SEQ ID NO:1 or functionally equivalent sequence thereof containing different codons for the same amino acid sequences.

2. A vaccine composition according to claim 1 wherein the recombinant YF virus is a virus recovered from a transfected cell culture of chicken embryo fibroblasts.

3. A vaccine composition according to claim 1 wherein the recombinant YF virus is present in said composition in an amount sufficient to induce immunity against said infection and wherein said composition further comprises a pharmaceutically acceptable carrier.

4. A vaccine composition according to claim 3 which further comprises a pharmaceutically acceptable stablizer.

5. A recombinant YF virus which is regenerated from YF infectious cDNA having the base sequence set forth in SEQ ID NO:1 or functionally equivalent sequence thereof containing different codons for the same amino acid sequences.

6. The recombinant YF virus according to claim 5 which is a virus recovered from a transfected cell culture of chicken embryo fibroblasts.

7. The recombinant YF virus according to claim 6 which is the Yfiv5.2/DD.

8. A method for producing recombinant YF virus comprising the step of:
   a. transfecting cells with YF infectious cDNA having the base sequence set forth in SEQ ID NO:1 or equivalents thereto containing different codons for the same amino acid sequences;
   b. culturing said cells under conditions sufficient for the cellular production of recombinant YF virus; and
   c. harvesting said recombinant YF virus which is a YF 17DD-like virus.

9. The method according to claim 8 wherein the YF infectious cDNA is the cDNA as set forth in SEQ ID NO:1.

10. The method according to claim 8 wherein the cells are selected from the group consisting of Hela (derived from carcinoma of human uterine cervix), CV-1 (derived from monkey kidney), BSC-1 (derived from monkey kidney), RK 13 (derived from rabbit kidney), L929 (derived from mouse connective tissue), CE (chicken embryo) cell, CEF (chicken embryo fibroblast), SW-13 (derived from human adrenocortical carcinoma), BHK-21 (baby hamster kidney), Vero (african green monkey kidney and LLC-MK2 (Rhesus monkey kidney (Macaca mulata)).

11. The method according to claim 8 wherein the cells are CEF.

12. The method according to claim 8 which is carried out under Good Manufacturing Practices (GMP).

13. An original seed lot comprising the YFiv5.2/DD which is produced according to claim 12.

14. A primary seed lot comprising the YFiv5.2/DD which is produced according to claim 12.

15. A secondary seed lot comprising the YFiv5.2/DD which is produced according to claim 12.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 10862 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (C) INDIVIDUAL ISOLATE: YFiv5.2/DD (xi) SEQUENCE DESCRIPTION: SEQ ID NO: 1:

```
AGTAAATCCT GTGTGCTAAT TGAGGTGCAT TGGTCTGCAA ATCGAGTTGC TAGGCAATAA      60

ACACATTTGG ATTAATTTTA ATCGTTCGTT GAGCGATTAG CAGAGAACTG ACCAGAACAT     120

GTCTGGTCGT AAAGCTCAGG GAAAAACCCT GGGCGTCAAT ATGGTACGAC GAGGAGTTCG     180

CTCCTTGTCA AACAAAATAA AACAAAAAAC AAAACAAATT GGAAACAGAC CTGGACCTTC     240

AAGAGGTGTT CAAGGATTTA TCTTTTTCTT TTTGTTCAAC ATTTTGACTG GAAAAAAGAT     300

CACAGCCCAC CTAAAGAGGT TGTGGAAAAT GCTGGACCCA AGACAAGGCT TGGCTGTTCT     360

AAGGAAAGTC AAGAGAGTGG TGGCCAGTTT GATGAGAGGA TTGTCCTCAA GGAAACGCCG     420

TTCCCATGAT GTTCTGACTG TGCAATTCCT AATTTTGGGA ATGCTGTTGA TGACGGGTGG     480

AGTGACCTTG GTGCGGAAAA ACAGATGGTT GCTCCTAAAT GTGACATCTG AGGACCTCGG     540

GAAAACATTC TCTGTGGGCA CAGGCAACTG CACAACAAAC ATTTTGGAAG CCAAGTACTG     600

GTGCCCAGAC TCAATGGAAT ACAACTGTCC CAATCTCAGT CCAAGAGAGG AGCCAGATGA     660

CATTGATTGC TGGTGCTATG GGGTGGAAAA CGTTAGAGTC GCATATGGTA AGTGTGACTC     720

AGCAGGCAGG TCTAGGAGGT CAAGAAGGGC CATTGACTTG CCTACGCATG AAAACCATGG     780

TTTGAAGACC CGGCAAGAAA AATGGATGAC TGGAAGAATG GGTGAAAGGC AACTCCAAAA     840

GATTGAGAGA TGGTTCGTGA GGAACCCCTT TTTTGCAGTG ACGGCTCTGA CCATTGCCTA     900

CCTTGTGGGA AGCAACATGA CGCAACGAGT CGTGATTGCC CTACTGGTCT TGGCTGTTGG     960

TCCGGCCTAC TCAGCTCACT GCATTGGAAT TACTGACAGG GATTTCATTG AGGGGGTGCA    1020
```

```
TGGAGGAACT TGGGTTTCAG CTACCCTGGA GCAAGACAAG TGTGTCACTG TTATGGCCCC    1080

TGACAAGCCT TCATTGGACA TCTCACTAGA GACAGTAGCC ATTGATAGAC CTGCTGAGGC    1140

GAGGAAAGTG TGTTACAATG CAGTTCTCAC TCATGTGAAG ATTAATGACA AGTGCCCCAG    1200

CACTGGAGAG GCCCACCTAG CTGAAGAGAA CGAAGGGGAC AATGCGTGCA AGCGCACTTA    1260

TTCTGATAGA GGCTGGGGCA ATGGCTGTGG CCTATTTGGG AAAGGGAGCA TTGTGGCATG    1320

CGCCAAATTC ACTTGTGCCA AATCCATGAG TTTGTTTGAG GTTGATCAGA CCAAAATTCA    1380

GTATGTCATC AGAGCACAAT TGCATGTAGG GGCCAAGCAG GAAAATTGGA ATACCAGCAT    1440

TAAGACTCTC AAGTTTGATG CCCTGTCAGG CTCCCAGGAA GTCGAGTTCA TTGGGTATGG    1500

AAAAGCTACA CTGGAATGCC AGGTGCAAAC TGCGGTGGAC TTTGGTAACA GTTACATCGC    1560

TGAGATGGAA ACAGAGAGCT GGATAGTGGA CAGACAGTGG GCCCAGGACT TGACCCTGCC    1620

ATGGCAGAGT GGAAGTGGCG GGGTGTGGAG AGAGATGCAT CATCTTGTCG AATTTGAACC    1680

TCCGCATGCC GCCACTATCA GAGTACTGGC CCTGGGAAAC CAGGAAGGCT CCTTGAAAAC    1740

AGCTCTTACT GGCGCAATGA GGGTTACAAA GGACACAAAT GACAACAACC TTTACAAACT    1800

ACATGGTGGA CATGTTTCTT GCAGAGTGAA ATTGTCAGCT TTGACACTCA AGGGGACATC    1860

CTACAAAATA TGCACTGACA AAATGTTTTT TGTCAAGAAC CCAACTGACA CTGGCCATGG    1920

CACTGTTGTG ATGCAGGTGA AAGTGCCAAA AGGAGCCCCC TGCAGGATTC CAGTGATAGT    1980

AGCTGATGAT CTTACAGCGG CAATCAATAA AGGCATTTTG GTTACAGTTA ACCCCATCGC    2040

CTCAACCAAT GATGATGAAG TGCTGATTGA GGTGAACCCA CCTTTTGGAG ACAGCTACAT    2100

TATCGTTGGG AGAGGAGATT CACGTCTCAC TTACCAGTGG CACAAAGAGG AAGCTCAAT    2160

AGGAAAGTTG TTCACTCAGA CCATGAAAGG CGTGGAACGC CTGGCCGTCA TGGGAGACGT    2220

CGCCTGGGAT TTCAGCTCCG CTGGAGGGTT CTTCACTTCG GTTGGGAAAG GAATTCATAC    2280

GGTGTTTGGC TCTGCCTTTC AGGGGCTATT TGGCGGCTTG AACTGGATAA CAAAGGTCAT    2340

CATGGGGGCG GTACTCATAT GGGTTGGCAT CAACACAAGA AACATGACAA TGTCCATGAG    2400

CATGATCTTG GTAGGAGTGA TCATGATGTT TTTGTCTCTA GGAGTTGGGG CGGATCAAGG    2460

ATGCGCCATC AACTTTGGCA AGAGAGAGCT CAAGTGCGGA GATGGTATCT TCATATTTAG    2520

AGACTCTGAT GACTGGCTGA ACAAGTACTC ATACTATCCA GAAGATCCTG TGAAGCTTGC    2580

ATCAATAGTG AAAGCCTCTT TCGAAGAAGG GAAGTGTGGC CTAAATTCAG TTGACTCCCT    2640

TGAGCATGAG ATGTGGAGAA GCAGGGCAGA TGAGATTAAT ACCATTTTTG AGGAAAACGA    2700

GGTGGACATT TCTGTTGTCG TGCAGGATCC AAAGAATGTT TACCAGAGAG GAACTCATCC    2760

ATTTTCCAGA ATTCGGGATG GTCTGCAGTA TGGTTGGAAG ACTTGGGGTA AGAACCTTGT    2820

GTTCTCCCCA GGGAGGAAGA ATGGAAGCTT CATCATAGAT GGAAAGTCCA GGAAAGAATG    2880

CCCGTTTTCA AACCGGGTCT GGAATTCTTT CCAGATAGAG GAGTTTGGGA CGGGAGTGTT    2940

CACCACACGC GTGTACATGG ACGCAGTCTT TGAATACACC ATAGACTGCG ATGGATCTAT    3000

CTTGGGTGCA GCGGTAACG GAAAAAAGAG TGCCCATGGC TCTCCAACAT TTTGGATGGG    3060

AAGTCATGAA GTAAATGGGA CATGGATGAT CCACACCTTG GAGGCATTAG ATTACAAGGA    3120

GTGTGAGTGG CCACTGACAC ATACGATTGG AACATCAGTT GAAGAGAGTG AAATGTTCAT    3180

GCCGAGATCA ATCGGAGGCC CAGTTAGCTC TCACAATCAT ATCCCTGGAT ACAAGGTTCA    3240

GACGAACGGA CCTTGGATGC AGGTACCACT AGAAGTGAAG AGAGAAGCTT GCCCAGGGAC    3300

TAGCGTGATC ATTGATGGCA ACTGTGATGG ACGGGGAAAA TCAACCAGAT CCACCACGGA    3360
```

```
TAGCGGGAAA GTTATTCCTG AATGGTGTTG CCGCTCCTGC ACAATGCCGC CTGTGAGCTT    3420

CCATGGTAGT GATGGGTGTT GGTATCCCAT GGAAATTAGG CCAAGGAAAA CGCATGAAAG    3480

CCATCTGGTG CGCTCCTGGG TTACAGCTGG AGAAATACAT GCTGTCCCTT TTGGTTTGGT    3540

GAGCATGATG ATAGCAATGG AAGTGGTCCT AAGGAAAAGA CAGGGACCAA AGCAAATGTT    3600

GGTTGGAGGA GTAGTGCTCT TGGGAGCAAT GCTGGTCGGG CAAGTAACTC TCCTTGATTT    3660

GCTGAAACTC ACAGTGGCTG TGGGATTGCA TTTCCATGAG ATGAACAATG GAGGAGACGC    3720

CATGTATATG GCGTTGATTG CTGCCTTTTC AATCAGACCA GGGCTGCTCA TCGGCTTTGG    3780

GCTCAGGACC CTATGGAGCC CTCGGGAACG CCTTGTGCTG ACCCTAGGAG CAGCCATGGT    3840

GGAGATTGCC TTGGGTGGCG TGATGGGCGG CCTGTGGAAG TATCTAAATG CAGTTTCTCT    3900

CTGCATCCTG ACAATAAATG CTGTTGCTTC TAGGAAAGCA TCAAATACCA TCTTGCCCCT    3960

CATGGCTCTG TTGACACCTG TCACTATGGC TGAGGTGAGA CTTGCCGCAA TGTTCTTTTG    4020

TGCCGTGGTT ATCATAGGGG TCCTTCACCA GAATTTCAAG GACACCTCCA TGCAGAAGAC    4080

TATACCTCTG GTGGCCCTCA CACTCACATC TTACCTGGGC TTGACACAAC CTTTTTTGGG    4140

CCTGTGTGCA TTTCTGGCAA CCCGCATATT TGGGCGAAGG AGTATCCCAG TGAATGAGGC    4200

ACTCGCAGCA GCTGGTCTAG TGGGAGTGCT GGCAGGACTG GCTTTTCAGG AGATGGAGAA    4260

CTTCCTTGGT CCGATTGCAG TTGGAGGACT CCTGATGATG CTGGTTAGCG TGGCTGGGAG    4320

GGTGGATGGG CTAGAGCTCA AGAAGCTTGG TGAAGTTTCA TGGGAAGAGG AGGCGGAGAT    4380

CAGCGGGAGT TCCGCCCGCT ATGATGTGGC ACTCAGTGAA CAAGGGGAGT TCAAGCTGCT    4440

TTCTGAAGAG AAAGTGCCAT GGGACCAGGT TGTGATGACC TCGCTGGCCT TGGTTGGGGC    4500

TGCCCTCCAT CCATTTGCTC TTCTGCTGGT CCTTGCTGGG TGGCTGTTTC ATGTCAGGGG    4560

AGCTAGGAGA AGTGGGGATG TCTTGTGGGA TATTCCCACT CCTAAGATCA TCGAGGAATG    4620

TGAACATCTG GAGGATGGGA TTTATGGCAT ATTCCAGTCA ACCTTCTTGG GGGCCTCCCA    4680

GCGAGGAGTG GGAGTGGCAC AGGGAGGGGT GTTCCACACA ATGTGGCATG TCACAAGAGG    4740

AGCTTTCCTT GTCAGGAATG GCAAGAAGTT GATTCCATCT TGGGCTTCAG TAAAGGAAGA    4800

CCTTGTCGCC TATGGTGGCT CATGGAAGTT GGAAGGCAGA TGGGATGGAG AGGAAGAGGT    4860

CCAGTTGATC GCGGCTGTTC CAGGAAAGAA CGTGGTCAAC GTCCAGACAA AACCGAGCTT    4920

GTTCAAAGTG AGGAATGGGG GAGAAATCGG GGCTGTCGCT CTTGACTATC CGAGTGGCAC    4980

TTCAGGATCT CCTATTGTTA ACAGGAACGG AGAGGTGATT GGGCTGTACG GCAATGGCAT    5040

CCTTGTCGGT GACAACTCCT TCGTGTCCGC CATATCCCAG ACTGAGGTGA AGGAAGAAGG    5100

AAAGGAGGAG CTCCAAGAGA TCCCGACAAT GCTAAAGAAA GGAATGACAA CTGTCCTTGA    5160

TTTTCATCCT GGAGCTGGGA AGACAAGACG TTTCCTCCCA CAGATCTTGG CCGAGTGCGC    5220

ACGGAGACGC TTGCGCACTC TTGTGTTGGC CCCCACCAGG GTTGTTCTTT CTGAAATGAA    5280

GGAGGCTTTT CACGGCCTGG ACGTGAAATT CCACACACAG CTTTTTCCG CTCACGGCAG    5340

CGGGAGAGAA GTCATTGATG CCATGTGCCA TGCCACCCTA ACTTACGGA TGTTGGAACC    5400

AACTAGGGTT GTTAACTGGG AAGTGATCAT TATGGATGAA GCCCATTTTT TGGATCCAGC    5460

TAGCATAGCC GCTAGAGGTT GGGCAGCGCA CAGAGCTAGG GCAAATGAAA GTGCAACAAT    5520

CTTGATGACA GCCACACCGC CTGGGACTAG TGATGAATTT CCACATTCAA ATGGTGAAAT    5580

AGAAGATGTT CAAACGGACA TACCCAGTGA GCCCTGGAAC ACAGGGCATG ACTGGATCCT    5640

AGCTGACAAA AGGCCCACGG CATGGTTCCT TCCATCCATC AGAGCTGCAA ATGTCATGGC    5700

TGCCTCTTTG CGTAAGGCTG GAAAGAGTGT GGTGGTCCTG AACAGGAAAA CCTTTGAGAG    5760
```

```
AGAATACCCC ACGATAAAGC AGAAGAAACC TGACTTTATA TTGGCCACTG ACATAGCTGA      5820

AATGGGAGCC AACCTTTGCG TGGAGCGAGT GCTGGATTGC AGGACGGCTT TTAAGCCTGT      5880

GCTTGTGGAT GAAGGGAGGA AGGTGGCAAT AAAAGGGCCA CTTCGTATCT CCGCATCCTC      5940

TGCTGCTCAA AGGAGGGGGC GCATTGGGAG AAATCCCAAC AGAGATGGAG ACTCATACTA      6000

CTATTCTGAG CCTACAAGTG AAAATAATGC CCACCACGTC TGCTGGTTGG AGGCCTCAAT      6060

GCTCTTGGAC AACATGGAGG TGAGGGGTGG AATGGTCGCC CCACTCTATG GCGTTGAAGG      6120

AACTAAAACA CCAGTTTCCC CTGGTGAAAT GAGACTGAGG GATGACCAGA GGAAAGTCTT      6180

CAGAGAACTA GTGAGGAATT GTGACCTGCC CGTTTGGCTT TCGTGGCAAG TGGCCAAGGC      6240

TGGTTTGAAG ACGAATGATC GTAAGTGGTG TTTTGAAGGC CCTGAGGAAC ATGAGATCTT      6300

GAATGACAGC GGTGAAACAG TGAAGTGCAG GGCTCCTGGA GGAGCAAAGA AGCCTCTGCG      6360

CCCAAGGTGG TGTGATGAAA GGGTGTCATC TGACCAGAGT GCGCTGTCTG AATTTATTAA      6420

GTTTGCTGAA GGTAGGAGGG GAGCTGCTGA AGTGCTAGTT GTGCTGAGTG AACTCCCTGA      6480

TTTCCTGGCT AAAAAAGGTG GAGAGGCAAT GGATACCATC AGTGTGTTTC TCCACTCTGA      6540

GGAAGGCTCT AGGGCTTACC GCAATGCACT ATCAATGATG CCTGAGGCAA TGACAATAGT      6600

CATGCTGTTT ATACTGGCTG GACTACTGAC ATCGGGAATG GTCATCTTTT TCATGTCTCC      6660

CAAAGGCATC AGTAGAATGT CTATGGCGAT GGGCACAATG GCCGGCTGTG GATATCTCAT      6720

GTTCCTTGGA GGCGTCAAAC CCACTCACAT CTCCTATATC ATGCTCATAT TCTTTGTCCT      6780

GATGGTGGTT GTGATCCCCG AGCCAGGGCA ACAAAGGTCC ATCCAAGACA ACCAAGTGGC      6840

ATACCTCATT ATTGGCATCC TGACGCTGGT TTCAGCGGTG GCAGCCAACG AGCTAGGCAT      6900

GCTGGAGAAA ACCAAGAGG ACCTCTTTGG GAAGAAGAAC TTAATTCCAT CTAGTGCTTC      6960

ACCCTGGAGT TGGCCGGATC TTGACCTGAA GCCAGGAGCT GCCTGGACAG TGTACGTTGG      7020

CATTGTTACA ATGCTCTCTC CAATGTTGCA CCACTGGATC AAAGTCGAAT ATGGCAACCT      7080

GTCTCTGTCT GGAATAGCCC AGTCAGCCTC AGTCCTTTCT TTCATGGACA AGGGGATACC      7140

ATTCATGAAG ATGAATATCT CGGTCATAAT GCTGCTGGTC AGTGGCTGGA ATTCAATAAC      7200

AGTGATGCCT CTGCTCTGTG GCATAGGGTG CGCCATGCTC CACTGGTCTC TCATTTTACC      7260

TGGAATCAAA GCGCAGCAGT CAAAGCTTGC ACAGAGAAGG GTGTTCCATG GCGTTGCCAA      7320

GAACCCTGTG GTTGATGGGA ATCCAACAGT TGACATTGAG GAAGCTCCTG AAATGCCTGC      7380

CCTTTATGAG AAGAAACTGG CTCTATATCT CCTTCTTGCT CTCAGCCTAG CTTCTGTTGC      7440

CATGTGCAGA ACGCCCTTTT CATTGGCTGA AGGCATTGTC CTAGCATCAG CTGCCTTAGG      7500

GCCGCTCATA GAGGGAAACA CCAGCCTTCT TTGGAATGGA CCCATGGCTG TCTCCATGAC      7560

AGGAGTCATG AGGGGGAATC ACTATGCTTT TGTGGGAGTC ATGTACAATC TATGGAAGAT      7620

GAAAACTGGA CGCCGGGGA GCGCGAATGG AAAAACTTTG GGTGAAGTCT GGAAGAGGGA      7680

ACTGAATCTG TTGGACAAGC GACAGTTTGA GTTGTATAAA AGGACCGACA TTGTGGAGGT      7740

GGATCGTGAT ACGGCACGCA GGCATTTGGC CGAAGGGAAG GTGGACACCG GGGTGGCGGT      7800

CTCCAGGGGG ACCGCAAAGT TAAGGTGGTT CCATGAGCGT GGCTATGTCA AGCTGGAAGG      7860

TAGGGTGATT GACCTGGGGT GTGGCCGCGG AGGCTGGTGT TACTACGCTG CTGCGCAAAA      7920

GGAAGTGAGT GGGGTCAAAG GATTTACTCT TGGAAGAGAC GGCCATGAGA AACCCATGAA      7980

TGTGCAAAGT CTGGGATGGA ACATCATCAC CTTCAAGGAC AAAACTGATA TCCACCGCCT      8040

AGAACCAGTG AAATGTGACA CCCTTTTGTG TGACATTGGA GAGTCATCAT CGTCATCGGT      8100
```

```
CACAGAGGGG GAAAGGACCG TGAGAGTTCT TGATACTGTA GAAAAATGGC TGGCTTGTGG      8160

GGTTGACAAC TTCTGTGTGA AGGTGTTAGC TCCATACATG CCAGATGTTC TCGAGAAACT      8220

GGAATTGCTC CAAAGGAGGT TTGGCGGAAC AGTGATCAGG AACCCTCTCT CCAGGAATTC      8280

CACTCATGAA ATGTACTACG TGTCTGGAGC CCGCAGCAAT GTCACATTTA CTGTGAACCA      8340

AACATCCCGC CTCCTGATGA GGAGAATGAG GCGTCCAACT GGAAAAGTGA CCCTGGAGGC      8400

TGACGTCATC CTCCCAATTG GGACACGCAG TGTTGAGACA GACAAGGGAC CCCTGGACAA      8460

AGAGGCCATA GAAGAAAGGG TTGAGAGGAT AAAATCTGAG TACATGACCT CTTGGTTTTA      8520

TGACAATGAC AACCCCTACA GGACCTGGCA CTACTGTGGC TCCTATGTCA CAAAAACCTC      8580

AGGAAGTGCG GCGAGCATGG TAAATGGTGT TATTAAAATT CTGACATATC CATGGGACAG      8640

GATAGAGGAG GTCACCAGAA TGGCAATGAC TGACACAACC CCTTTTGGAC AGCAAAGAGT      8700

GTTTAAAGAA AAAGTTGACA CCAGAGCAAA GGATCCACCA GCGGGAACTA GGAAGATCAT      8760

GAAAGTTGTC AACAGGTGGC TGTTCCGCCA CCTGGCCAGA GAAAAGAGCC CCAGACTGTG      8820

CACAAAGGAA GAATTTATTG CAAAAGTCCG AAGTCATGCA GCCATTGGAG CTTACCTGGA      8880

AGAACAAGAA CAGTGGAAGA CTGCCAATGA GGCTGTCCAA GACCCAAAGT TCTGGGAACT      8940

GGTGGATGAA GAAAGGAAGC TGCACCAACA AGGCAGGTGT CGGACTTGTG TGTACAACAT      9000

GATGGGAAAA AGAGAGAAGA AGCTGTCAGA GTTTGGGAAA GCAAAGGGAA GCCGTGCCAT      9060

ATGGTATATG TGGCTGGGAG CGCGGTATCT TGAGTTTGAG GCCCTGGGAT TCCTGAATGA      9120

GGACCATTGG GCTTCCAGGG AAAACTCAGG AGGAGGAGTG GAAGGCATTG GCTTACAATA      9180

CCTAGGATAT GTGATCAGAG ACCTGGCTGC AATGGATGGT GGTGGATTCT ACGCGGATGA      9240

CACCGCTGGA TGGGACACGC GCATCACAGA GGCAGACCTT GATGATGAAC AGGAGATCTT      9300

GAACTACATG AGCCCACATC ACAAAAAACT GGCACAAGCA GTGATGGAAA TGACATACAA      9360

GAACAAAGTG GTGAAAGTGT TGAGACCAGC CCCAGGAGGG AAAGCCTACA TGGATGTCAT      9420

AAGTCGACGA GACCAGAGAG GATCCGGGCA GGTAGTGACT TATGCTCTGA ACACCATCAC      9480

CAACTTGAAA GTCCAATTGA TCAGAATGGC AGAAGCAGAG ATGGTGATAC ATCACCAACA      9540

TGTTCAAGAT TGTGATGAAT CAGTTCTGAC CAGGCTGGAG GCATGGCTCA CTGAGCACGG      9600

ATGTAACAGA CTGAAGAGGA TGGCGGTGAG TGGAGACGAC TGTGTGGTCC GGCCCATCGA      9660

TGACAGGTTC GGCCTGGCCC TGTCCCATCT CAACGCCATG TCCAAGGTTA GAAAGGACAT      9720

ATCTGAATGG CAGCCATCAA AAGGGTGGAA TGATTGGGAA AATGTGCCCT TCTGTTCCCA      9780

CCACTTCCAT GAACTACAGC TGAAGGATGG CAGGAGGATT GTGGTGCCTT GCCGAGAACA      9840

GGACGAGCTC ATTGGGAGAG AAGGGTGTC TCCAGGAAAC GGCTGGATGA TCAAGGAAAC      9900

AGCTTGCCTC AGCAAAGCCT ATGCCAACAT GTGGTCACTG ATGTATTTTC ACAAAAGGGA      9960

CATGAGGCTA CTGTCATTGG CTGTTTCCTC AGCTGTTCCC ACCTCATGGG TTCCACAAGG      10020

ACGCACAACA TGGTCGATTC ATGGGAAAGG GGAGTGGATG ACCACGGAAG ACATGCTTGA      10080

GGTGTGGAAC AGAGTATGGA TAACCAACAA CCCACACATG CAGGACAAGA CAATGGTGAA      10140

AAAATGGAGA GATGTCCCTT ATCTAACCAA GAGACAAGAC AAGCTGTGCG GATCACTGAT      10200

TGGAATGACC AATAGGGCCA CCTGGGCCTC CCACATCCAT TTAGTCATCC ATCGTATCCG      10260

AACGCTGATT GGACAGGAGA AATACACTGA CTACCTAACA GTCATGGACA GGTATTCTGT      10320

GGATGCTGAC CTGCAACTGG GTGAGCTTAT CTGAAACACC ATCTAACAGG AATAACCGGG      10380

ATACAAACCA CGGGTGGAGA ACCGGACTCC CCACAACCTG AAACCGGGAT ATAAACCACG      10440

GCTGGAGAAC CGGACTCCGC ACTTAAAATG AAACAGAAAC CGGGATAAAA ACTACGGATG      10500
```

```
                                        -continued

GAGAACCGGA CTCCACACAT TGAGACAGAA GAAGTTGTCA GCCCAGAACC CCACACGAGT    10560

TTTGCCACTG CTAAGCTGTG AGGCAGTGCA GGCTGGGACA GCCGACCTCC AGGTTGCGAA    10620

AAACCTGGTT TCTGGGACCT CCCACCCCAG AGTAAAAAGA ACGGAGCCTC CGCTACCACC    10680

CTCCCACGTG GTGGTAGAAA GACGGGGTCT AGAGGTTAGA GAAGACCCTC CAGGGAACAA    10740

ATAGTGGGAC CATATTGACG CCAGGGAAAG ACCGGAGTGG TTCTCTGCTT TTCCTCCAGA    10800

GGTCTGTGAG CACAGTTTGC TCAAGAATAA GCAGACCTTT GGATGACAAA CACAAAACCA    10860

CT                                                                   10862
```